US011364144B2

(12) United States Patent
Jackson et al.

(10) Patent No.: US 11,364,144 B2
(45) Date of Patent: Jun. 21, 2022

(54) APPARATUS FOR THE MOISTURE, MEDICATED, AND THERMAL TREATMENT OF PHYSICAL CONDITIONS

(71) Applicants: Rachel E. Jackson, Buffalo, NY (US); Angelo Caico, Buffalo, NY (US)

(72) Inventors: Rachel E. Jackson, Buffalo, NY (US); Angelo Caico, Buffalo, NY (US)

( * ) Notice: Subject to any disclaimer, the term of this patent is extended or adjusted under 35 U.S.C. 154(b) by 664 days.

(21) Appl. No.: 15/986,587

(22) Filed: May 22, 2018

(65) Prior Publication Data

US 2019/0358440 A1 Nov. 28, 2019

(51) Int. Cl.
| | | |
|---|---|---|
| *A61F 7/08* | (2006.01) | |
| *A61F 7/00* | (2006.01) | |
| *A61F 9/00* | (2006.01) | |
| *A61M 35/00* | (2006.01) | |
| *A61F 7/02* | (2006.01) | |

(52) U.S. Cl.
CPC .............. *A61F 7/08* (2013.01); *A61F 9/0026* (2013.01); *A61F 2007/0004* (2013.01); *A61F 2007/005* (2013.01); *A61F 2007/023* (2013.01); *A61F 2007/0261* (2013.01); *A61M 35/00* (2013.01); *A61M 2205/36* (2013.01); *A61M 2209/088* (2013.01); *A61M 2210/1483* (2013.01)

(58) Field of Classification Search
CPC ...... A61F 7/00; A61F 7/02; A61F 7/08; A61F 2007/0028; A61F 2007/0048; A61F 2007/005; A61F 2007/0236; A61F 2007/0261; A61F 2007/0228; A61F 2007/023; A61F 2007/0244; A61F 2007/0268; A61F 2007/0238; A61F 2007/0217; A61F 2007/0219; A61F 2007/0002; A61F 2007/0004; A61F 2007/0225; A61F 9/04; A61F 13/47218; A61F 13/47209; A61F 13/47227; A61F 13/51113; A61F 13/51117; A61F 13/00063; A61F 13/8405; A61F 2013/8432; A61F 2013/8435; A61F 2013/00646; A61F 5/0093; A61F 13/15268; A61F 13/49003; A61F 2007/0279; A61F 13/47263; A61F 13/47245; A61F 13/47272; A61M 35/00; A61M 35/10; A61M 2210/1483; A61M 2205/36; A61L 15/44
See application file for complete search history.

(56) References Cited

U.S. PATENT DOCUMENTS

| | | |
|---|---|---|
| 2,043,325 A | 6/1936 | Jackson, Jr. |
| 3,175,558 A | 3/1965 | Caillouette et al. |
| 3,871,376 A | 3/1975 | Kozak |

(Continued)

FOREIGN PATENT DOCUMENTS

WO WO-2014077482 A1 * 5/2014 ............. A61L 15/42

*Primary Examiner* — Susan S Su
(74) *Attorney, Agent, or Firm* — Simpson & Simpson, PLLC

(57) ABSTRACT

An assembly for the thermal treatment and moisture treatment of physical conditions, the assembly including, a first thermal pack having a body, the body having a first face and a second face, the first face having a first protrusion. The assembly further includes a sleeve operatively arranged to receive the first thermal pack, the sleeve having a first surface. The assembly also includes a medicament pad arranged to be removably secured to the first surface of the sleeve.

17 Claims, 20 Drawing Sheets

(56) References Cited

U.S. PATENT DOCUMENTS

| | | | |
|---|---|---|---|
| 4,240,436 A | 12/1980 | Singleton | |
| 4,660,238 A | 4/1987 | Jay | |
| 4,700,706 A * | 10/1987 | Munch | A61F 7/10 |
| | | | 604/113 |
| 4,709,431 A | 12/1987 | Shaktman | |
| 4,834,739 A | 5/1989 | Linker, III et al. | |
| 4,844,073 A | 7/1989 | Pohler | |
| 4,910,978 A | 3/1990 | Gordon et al. | |
| 4,932,397 A | 6/1990 | McFaul, Sr. | |
| 5,062,425 A | 11/1991 | Tucker | |
| 5,094,238 A | 3/1992 | Gibbon | |
| D327,329 S | 6/1992 | Hubbard et al. | |
| 5,167,655 A | 12/1992 | McCoy | |
| 5,178,139 A | 1/1993 | Angelillo et al. | |
| 5,190,033 A | 3/1993 | Johnson | |
| 5,234,914 A | 8/1993 | Gallina | |
| 5,274,865 A * | 1/1994 | Takehashi | A61F 7/10 |
| | | | 5/643 |
| 5,393,462 A | 2/1995 | Avery | |
| 5,707,645 A | 1/1998 | Wierson | |
| 5,792,213 A | 8/1998 | Bowen | |
| 5,843,145 A | 12/1998 | Brink | |
| 5,935,595 A * | 8/1999 | Steen | A61F 7/10 |
| | | | 424/443 |
| 5,989,286 A | 11/1999 | Owens | |
| 6,074,415 A | 6/2000 | Der Ovanesian | |
| 6,083,256 A | 7/2000 | Der Ovanesian | |
| 6,156,323 A | 12/2000 | Verdicchio et al. | |
| 6,251,131 B1 | 1/2001 | Kohout | |
| D437,642 S | 2/2001 | Caballero | |
| 6,226,820 B1 | 5/2001 | Navarro | |
| 6,248,125 B1 | 6/2001 | Helming | |
| 6,320,095 B1 | 11/2001 | Wall | |
| D477,076 S | 7/2003 | Wall | |
| 6,716,229 B2 | 4/2004 | Toth | |
| 6,786,880 B2 | 9/2004 | Wall | |
| D520,137 S | 5/2006 | Melendez et al. | |
| D537,161 S | 2/2007 | Sinkiewicz | |
| 7,288,080 B2 | 10/2007 | Edens et al. | |
| 7,291,136 B1 | 11/2007 | Drevik et al. | |
| 7,344,196 B2 | 3/2008 | Rodriquez | |
| 7,615,675 B2 | 11/2009 | Roe et al. | |
| 7,686,793 B2 | 3/2010 | Mizutani et al. | |
| 7,784,304 B2 | 8/2010 | Trinh et al. | |
| 7,937,212 B2 | 5/2011 | Hori | |
| 8,123,760 B2 | 2/2012 | Blurton | |
| 8,247,637 B2 | 8/2012 | Renzin et al. | |
| D667,129 S | 9/2012 | Shelton | |
| 8,696,727 B2 | 4/2014 | Emon | |
| 8,747,377 B2 | 6/2014 | Renzin et al. | |
| D764,675 S | 8/2016 | Peisner et al. | |
| 9,572,709 B2 | 2/2017 | Fogg | |
| 9,592,150 B2 | 3/2017 | McNulty, Jr. | |
| 9,687,386 B2 | 6/2017 | Carson | |
| 9,713,351 B2 | 7/2017 | Wexler | |
| 2002/0065497 A1 | 5/2002 | Kolby-Falk | |
| 2002/0193026 A1 * | 12/2002 | Ota | A61K 8/0208 |
| | | | 442/261 |
| 2004/0162537 A1 * | 8/2004 | Manasek | A61F 13/45 |
| | | | 604/385.01 |
| 2005/0261755 A1 | 11/2005 | Bacino et al. | |
| 2005/0267435 A1 * | 12/2005 | Tanio | A61F 13/47272 |
| | | | 604/385.17 |
| 2007/0021809 A1 | 1/2007 | Cole et al. | |
| 2007/0106356 A1 * | 5/2007 | Carstens | A62B 23/00 |
| | | | 607/112 |
| 2008/0033384 A1 * | 2/2008 | Renzin | A61F 13/8405 |
| | | | 604/364 |
| 2008/0039810 A1 | 2/2008 | Lee et al. | |
| 2008/0071336 A1 * | 3/2008 | Merriman | A61F 7/10 |
| | | | 607/113 |
| 2008/0275534 A1 | 11/2008 | Noel | |
| 2008/0312630 A1 * | 12/2008 | Seo | A61F 13/505 |
| | | | 604/385.03 |
| 2009/0076575 A1 | 3/2009 | Noel | |
| 2009/0131889 A1 | 5/2009 | Oronsky et al. | |
| 2011/0166635 A1 * | 7/2011 | Nelson | A61F 7/02 |
| | | | 607/112 |
| 2013/0023970 A1 | 1/2013 | Cull | |
| 2014/0371828 A1 * | 12/2014 | Whitely | A61F 7/106 |
| | | | 607/108 |
| 2015/0018763 A1 | 1/2015 | Lee | |
| 2017/0079836 A1 | 3/2017 | Mahon | |

* cited by examiner

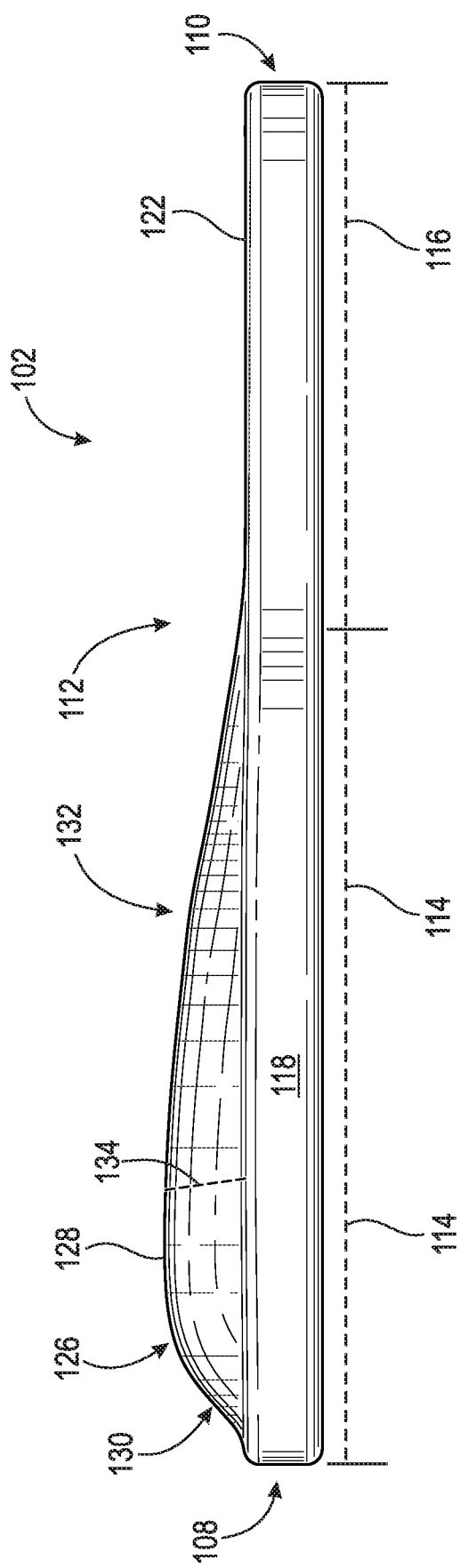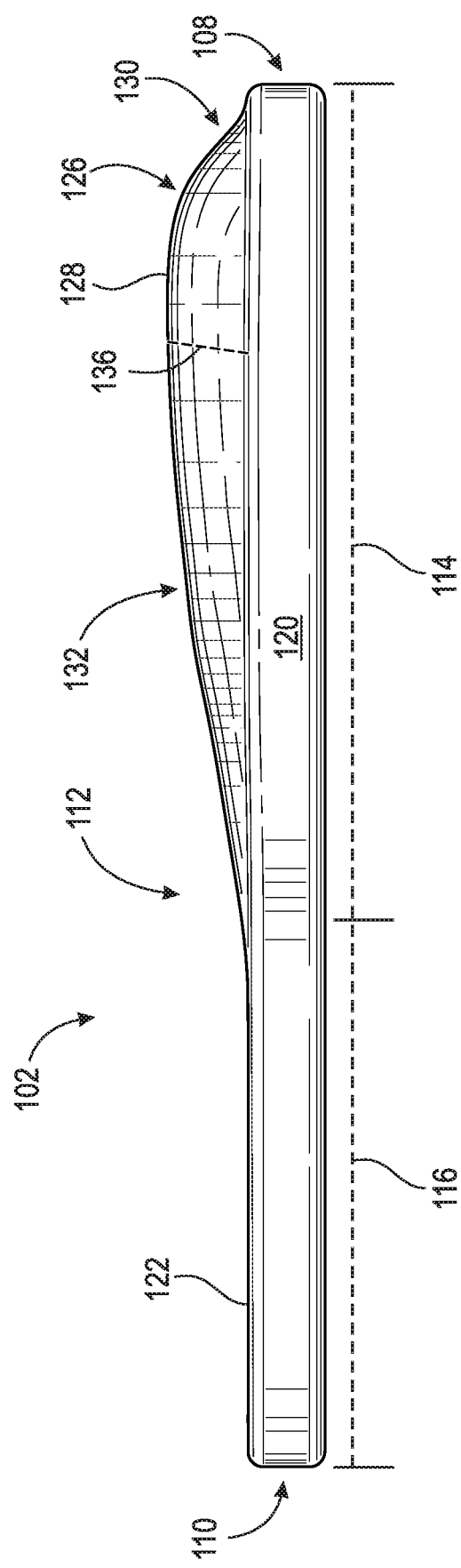

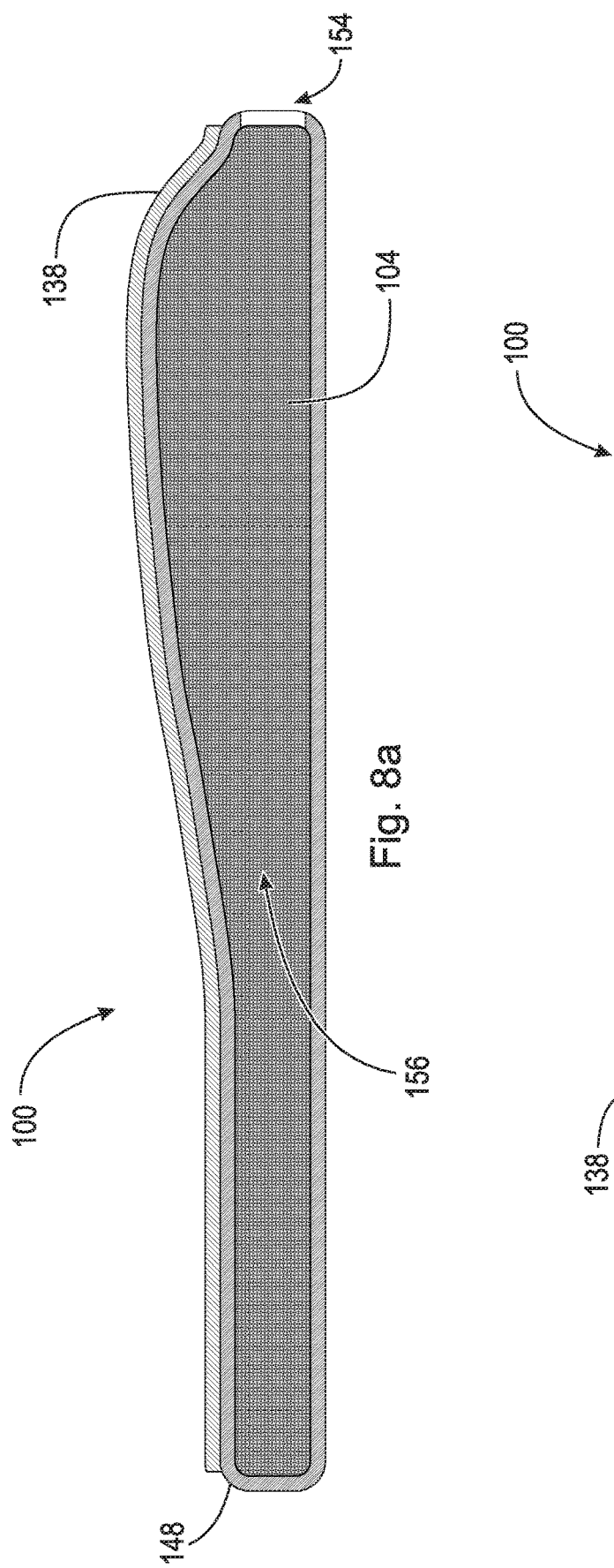
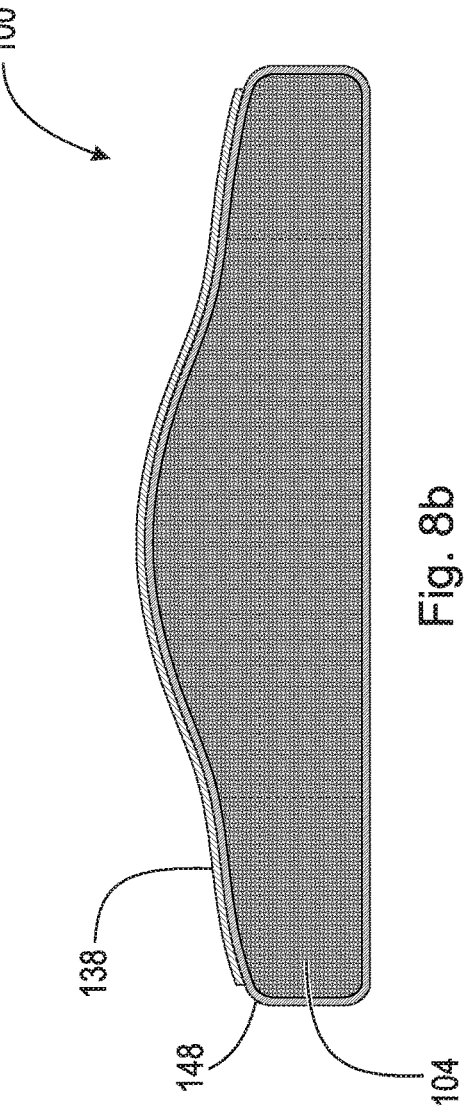

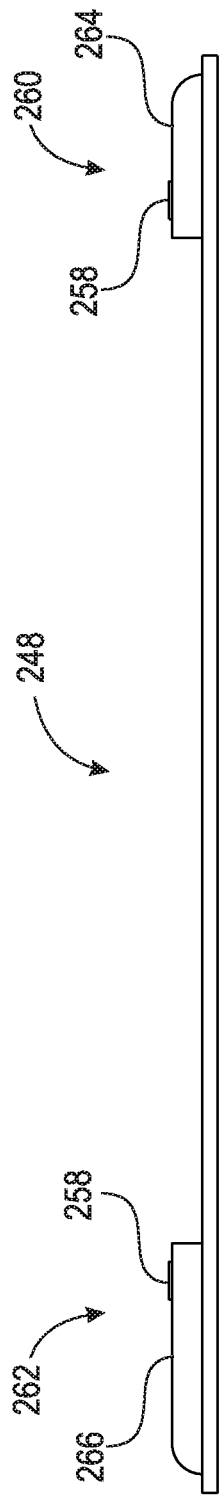
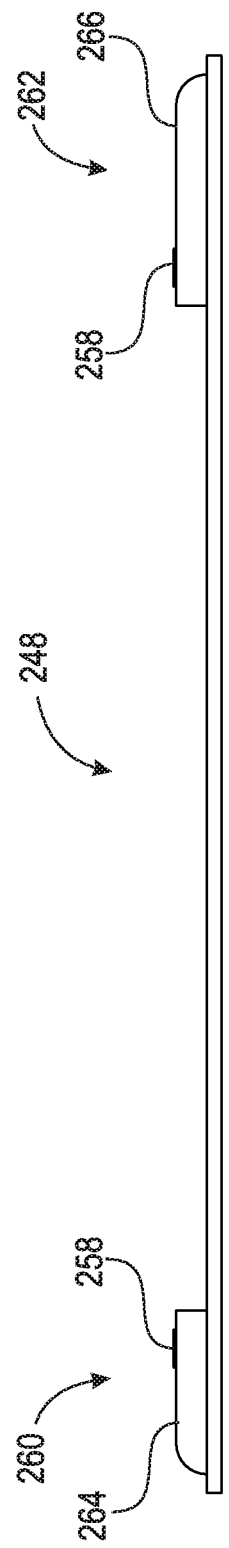
Fig. 12a
Fig. 12b

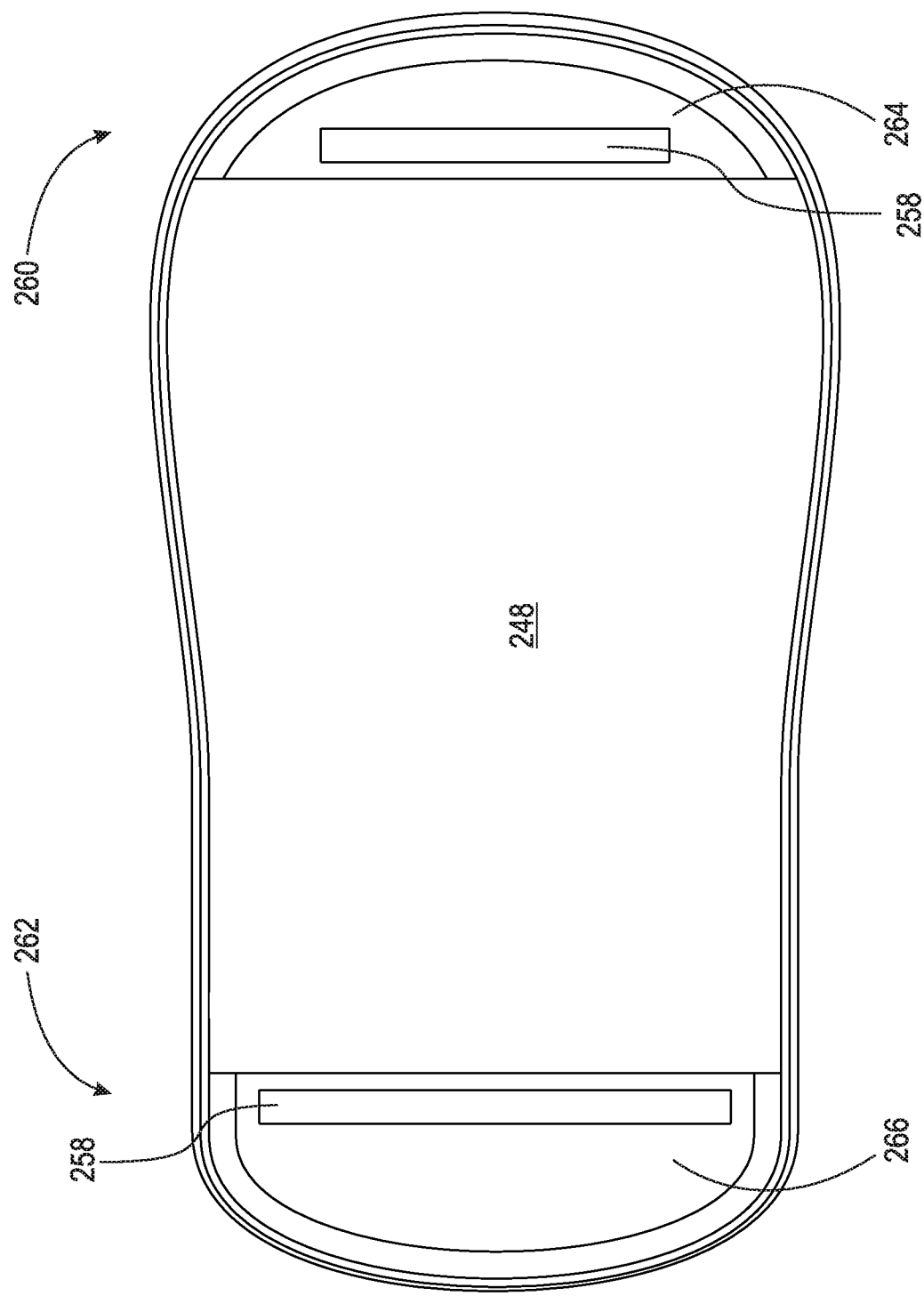

APPARATUS FOR THE MOISTURE, MEDICATED, AND THERMAL TREATMENT OF PHYSICAL CONDITIONS

FIELD OF THE INVENTION

The present invention broadly relates to a device for the moisture treatment, medicated treatment, and/or thermal treatment of symptoms associated with physical conditions, more particularly to a medicated device for the moisture and thermal treatment of perineal conditions and/or the moisture and thermal treatment of ophthalmological conditions.

BACKGROUND OF THE INVENTION

Thermal devices are well known in the art. Both heating and icing, also known as thermotherapy and cryotherapy, respectively, can be effective remedies for treating various ailments. For example, ice is used to calm damaged tissues that are inflamed, red, hot and swollen as inflammation can be incredibly painful and persistent. Ice is commonly used as part of the initial treatment for sprains and strains, and other injuries. In particular, cold slows down blood flow to an injury, thereby reducing pain and swelling. Cryotherapy slows circulation, reducing inflammation, muscle spasm, and pain.

Conversely, heat is used to ease the pain of muscle spasms and trigger points, or conditions that are often dominated by them, like back and neck pain. Heat is generally recommended for chronic aches and pains, or new and minor muscular pains. Muscles tend to relax under thermotherapy as the heat can help improve circulation, reduce muscle spasms, and increase range of motion. In particular, heat opens up blood vessels, which increases blood flow and supplies oxygen and nutrients to areas of the body that require therapy. One problem with heating and cooling is that too much of either type of thermal therapy can harm skin and damage tissue.

The recovery from certain elective surgeries like a vasectomy, or non-elective surgical procedures such as episiotomies, may be aided with the application hot/cold therapy. These areas of the body are exposed to heightened levels of bacteria and require a hygienic application of hot/cold therapy to reduce risk of further trauma cause by infection.

Thus, there is a long-felt need for an assembly for the moisture treatment, medicated treatment, and/or thermal treatment of physical conditions such as, vasectomy, episiotomy, hemorrhoids, ingrown hairs, or other conditions that effect the perineal or orbital area of the human body.

BRIEF SUMMARY OF THE INVENTION

According to aspects illustrated herein, there is provided a thermal pack for the thermal treatment of physical conditions. The thermal pack including a body, the body having a first end, a second end, a middle, a first portion arranged between the first end and the middle, a second portion arranged between the second end and the middle, a first side, a second side, a first face, the first face having a first surface, a second face, the second face having a second surface, the second surface being substantially planer, and a first protrusion arranged on the first surface of the first face and within the first portion.

According to aspects illustrated herein, there is provided an assembly for the thermal treatment, moisture treatment, and/or medicated treatment of physical conditions, the assembly including, a first thermal pack having a body, the body having a first face and a second face. The assembly further includes a sleeve operatively arranged to receive the first thermal pack, the sleeve having a first surface. The assembly also includes a medicament pad arranged to be removably secured to the first surface of the sleeve.

These and other objects, advantages and features of the present invention will be better appreciated by those having ordinary skill in the art in view of the following detailed description of the invention in view of the drawings.

BRIEF DESCRIPTION OF THE DRAWINGS

The nature and mode of operation of the present invention will now be more fully described in the following detailed description of the invention taken with the accompanying drawing figures, in which:

FIG. 4a is a left side elevational view of a device for the thermal treatment of physical conditions as disclosed herein;

FIG. 4b is a right side elevational view of a device for the thermal treatment of physical conditions as disclosed herein;

FIG. 8a is a right side cross-sectional view of an assembly for the thermal treatment, moisture treatment, and/or medicated treatment of physical conditions taken generally along line 8a-8a in FIG. 6a;

FIG. 8b is a rear side cross-sectional view of an assembly for the thermal treatment, moisture treatment, and/or medicated treatment of physical conditions taken generally along line 8b-8b in FIG. 7b;

FIG. 12a is a right side elevational view of a sleeve as used in an assembly for the thermal treatment, moisture treatment, and/or medicated treatment of physical conditions as disclosed herein;

FIG. 12b is a left side elevational view of a sleeve as used in an assembly for the thermal treatment, moisture treatment, and/or medicated treatment of physical conditions as disclosed herein;

FIG. 13 is a top plan view of a sleeve as used in an assembly for the thermal treatment, moisture treatment, and/or medicated treatment of physical conditions as disclosed herein;

DETAILED DESCRIPTION OF THE INVENTION

At the outset, it should be appreciated that like drawing numbers on different drawing views identify identical, or functionally similar, structural root elements of the invention. Moreover, although any methods, devices or materials similar or equivalent to those described herein can be used in the practice or testing of these embodiments, some embodiments of methods, devices, and materials are now described.

Furthermore, it is understood that this invention is not limited to the particular methodology, materials and modifications described and, as such, may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. It should be appreciated that the term "substantially" is synonymous with terms such as "nearly", "very nearly", "about", "approximately", "around", "bordering on", "close to", "essentially", "in the neighborhood of", "in the vicinity of", etc., and such terms may be used interchangeably as appearing in the specification and claims. Additionally, the term "thermal" is defined as "being or involving a state of matter dependent upon temperature," and thus, may be used interchangeably with reference to an element that can be "heated" or "cooled," as appearing in the specification and claims. Although any methods, devices or materials similar or equivalent to those described herein can be used in the practice or testing of the invention, the preferred methods, devices, and materials are now described.

Figure 1:
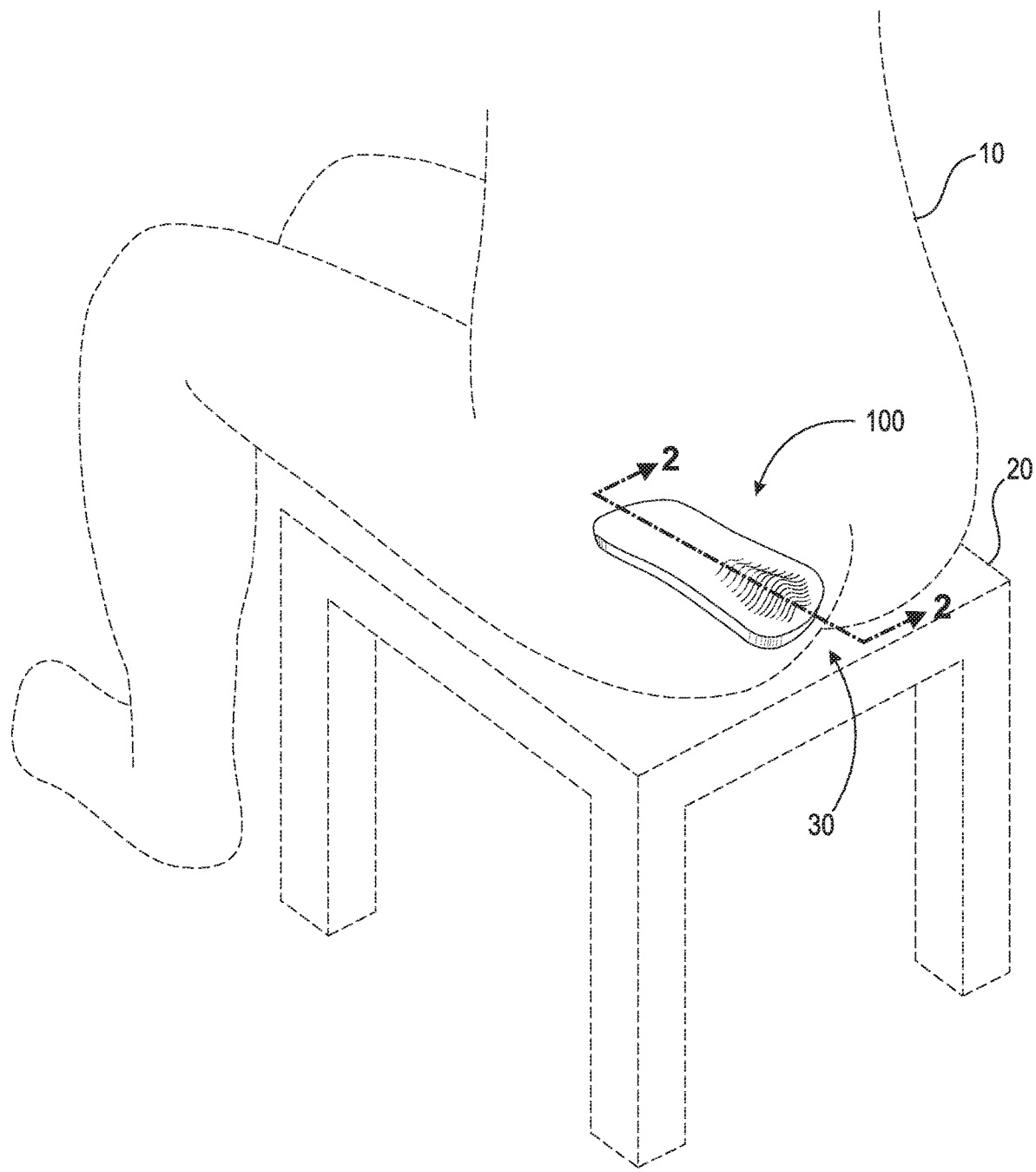
FIG. 1 is a rear perspective view of a device for the thermal treatment of physical conditions as described herein applied to a user.
Figure 2:
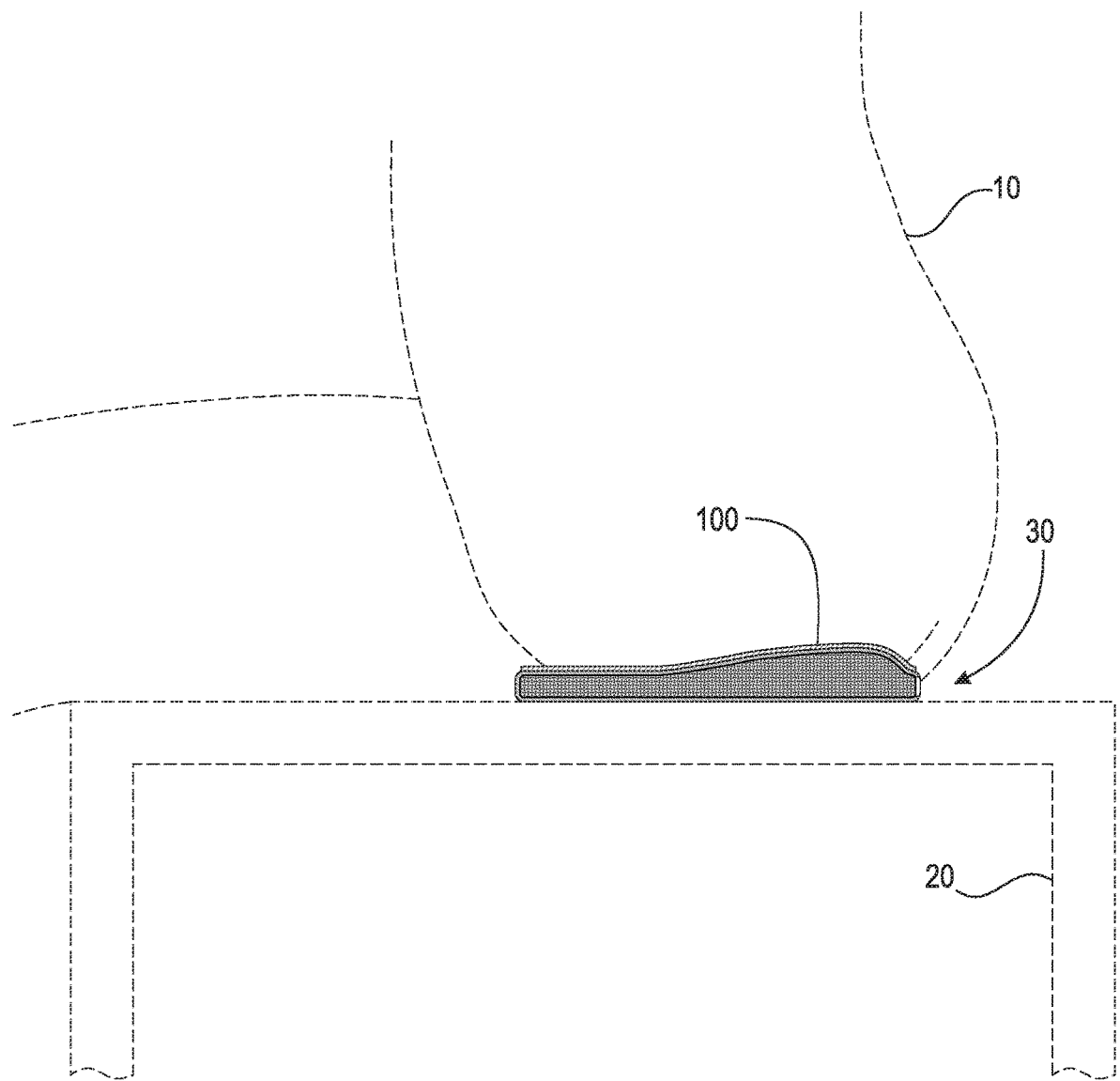
FIG. 2 is cross-section view of a device for the thermal treatment of physical conditions, taken generally along line 2-2 in FIG. 1.

Adverting now to the figures, FIG. 1 illustrates the inventive device in context, i.e., user 10 sitting on chair 20 where assembly 100 is secured beneath user 10 and in a position to provided medicated, moisture, and/or thermal therapy to perineal area 30. The various components included in assembly 100 will be discussed in detail infra. FIG. 2 illustrates a cross-sectional view along line 2-2 shown in FIG. 1.

Figure 3:
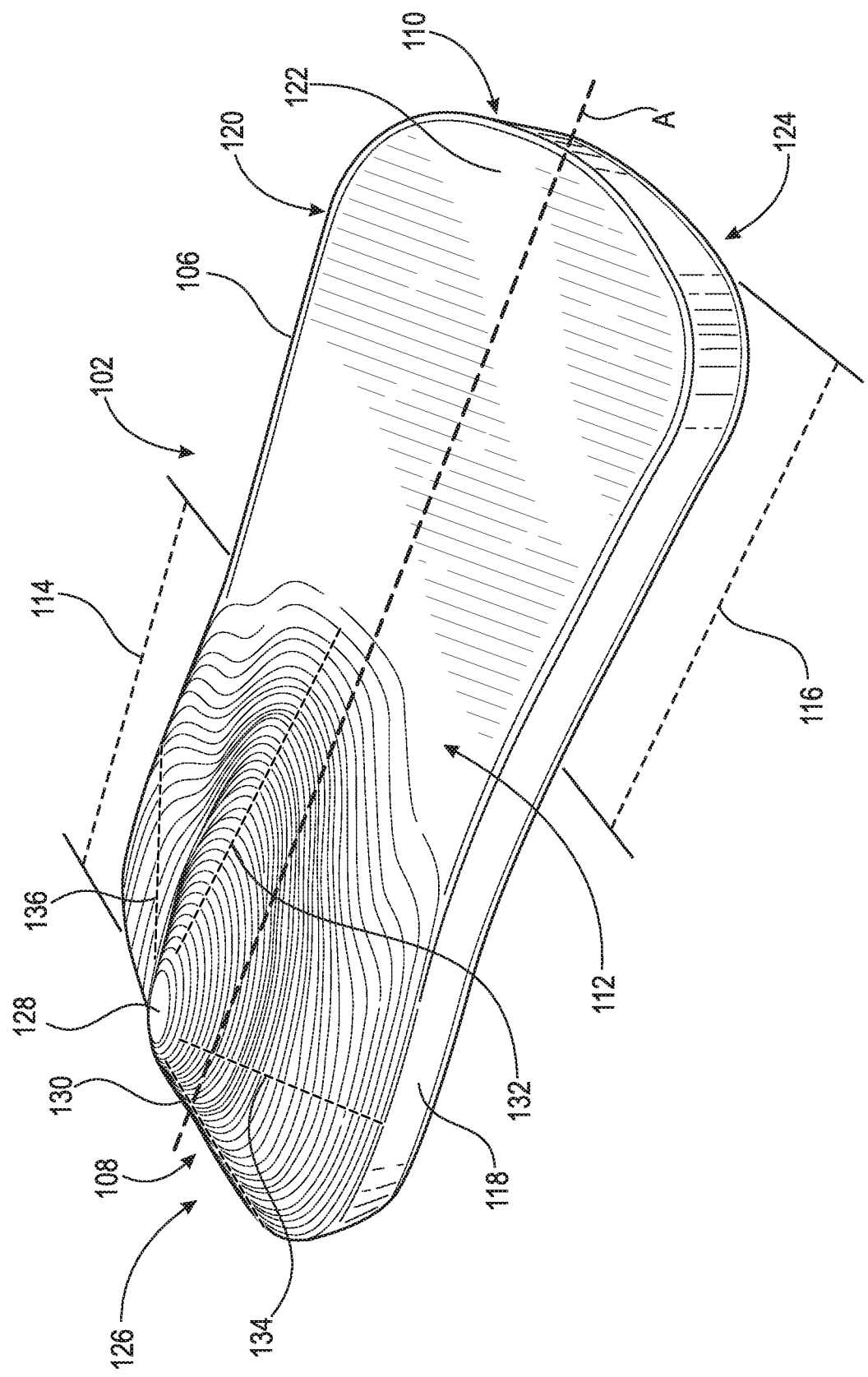
FIG. 3 is a front side perspective view of a device for the thermal treatment of physical conditions as disclosed herein.

The following should be read in view of FIGS. 3-4b. Assembly 100 includes thermal pack 102. Thermal pack 102 includes thermal material 104 (shown in FIGS. 8a and 8b) within body 106. Thermal material 104 can include but is not limited to materials such as thermally conductive silica gel, ceramic beads, glass beads, vinyl-based synthetic beads, sodium acetate, sodium polyacrylate, hydroxyethyl cellulose, paraffin, rice, flax seed, barley, corn, buckwheat, etc. Body 106 has first end 108, second end 110, middle 112, first portion 114, and second portion 116. First portion 114 is defined by the part of body 106 between middle 112 and first end 108. Second portion 116 is defined by the part of body 106 between middle 112 and second end 110. Body 106 further includes first side 118, second side 120, first face 122 and second face 124. First side 118 is substantially perpendicular to first face 122 and co-terminus with axis A. Second side 120 is substantially perpendicular to first face 122, co-terminus with axis A, and disposed opposite first side 118. On first face 122, and within the first portion 114, body 106 further includes first protrusion 126.

Protrusion 126 is designed to complement, by forming the anatomical negative of, the various areas of the human body where assembly 100 can be utilized. As used herein, "anatomical negative" is intended to mean the reverse, inverted, or opposite form of the natural anatomical structure of the areas of the perineum. For example, when applied to the perineal area closest to the human anus, the shape of protrusion 126 is intended to nestle between the cheeks of the buttocks and extend the heating and cooling capabilities of thermal pack 102 to the anal sphincter for the treatment of hemorrhoids. Alternatively, if used post-episiotomy, protrusion 126 is intended to nestle between the labia majora or labia minora of a female user to extend the heating and cooling capabilities to the affected area. It should also be appreciated that assembly 100 can be utilized in other applications, e.g., post-surgery hot/cold therapy for vasectomies, for application to ingrown hairs, and/or for soothing pre-childbirth and post-childbirth pains such as soothing of the perineum.

To achieve this effect, protrusion 126 is defined by apex 128, first slope 130, second slope 132, third slope 134, and fourth slope 136. Apex 128 is the highest point on protrusion 128. First slope 130 is defined by a gradual height gradient with respect to first face 122 starting at apex 128 and terminating at the edge of first face 122 proximate first end 108. Second slope 132 is defined by a gradual height gradient with respect to first face 122 starting at apex 128 and terminating at the edge of first portion 114 proximate middle 112 of body 106. The height gradient of first slope 130 is substantially larger, i.e., steeper, than the height gradient of second slope 132. Third slope 134 is defined by a gradual height gradient with respect to first face 122 starting at apex 128 and terminating at the junction of first side 118 and first face 122. Fourth slope 136 is defined by a gradual height gradient with respect to first face 122 starting at apex 128 and terminating at the junction of second side 120 and first face 122. The height gradient of third slope 134 and fourth slope 136 are intended to be substantially similar, i.e., symmetrical; however, it should be appreciated that the height gradients of both third slope 134 and fourth slope 136 do not have to be equal. Additionally, the height gradient of third slope 134 and fourth slope 136, are intended to be larger, i.e., steeper than second slope 132 but smaller, i.e., less steep than first slope 130. The shape of protrusion 126, via slopes 130-134 is intended to be the anatomical negative of the human anus so as to provide user 10, when sitting on assembly 100, with heating/cooling therapy to the entire perineal area including for example, the anus.

Figure 5:
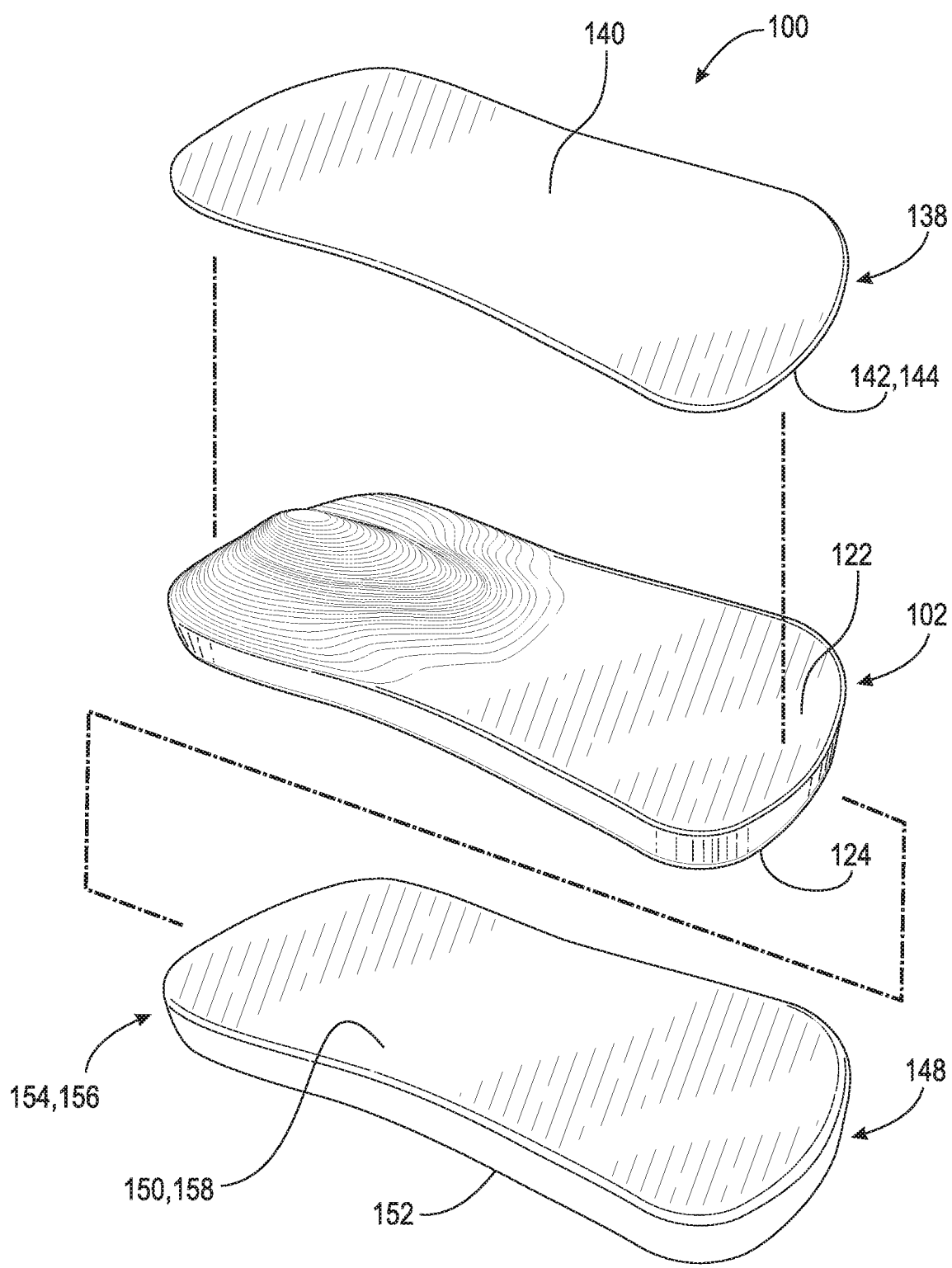
FIG. 5 is an exploded perspective view of an assembly for the thermal treatment, moisture treatment, and/or medicated treatment of physical conditions as disclosed herein.
Figure 6A:
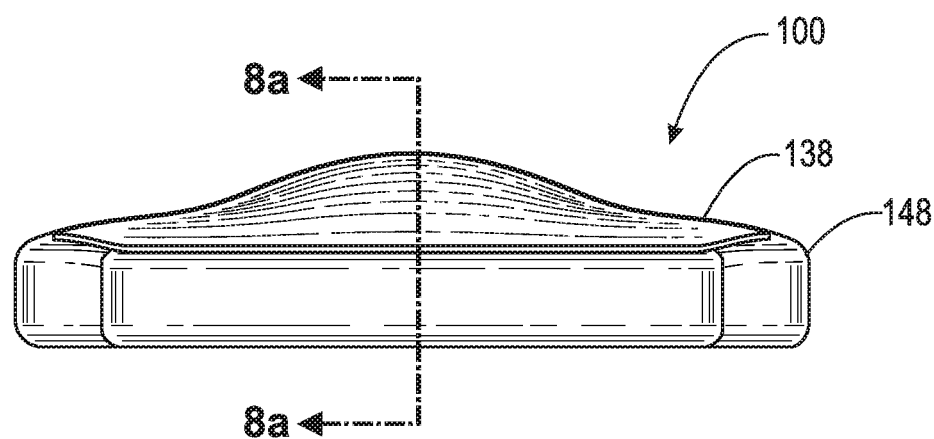
FIG. 6a is a front side elevational view of an assembly for the thermal treatment, moisture treatment, and/or medicated treatment of physical conditions as disclosed herein.
Figure 6B:
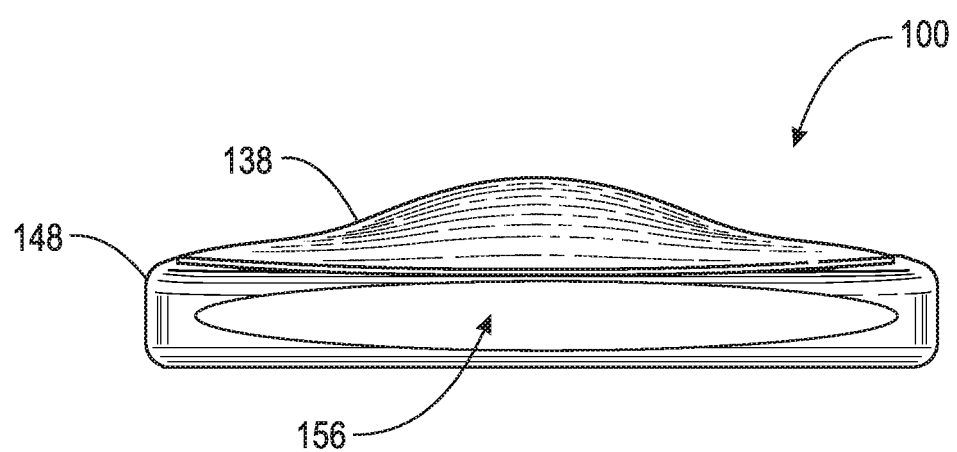
FIG. 6b is a rear side elevational view of an assembly for the thermal treatment, moisture treatment, and/or medicated treatment of physical conditions as disclosed herein.
Figure 7A:
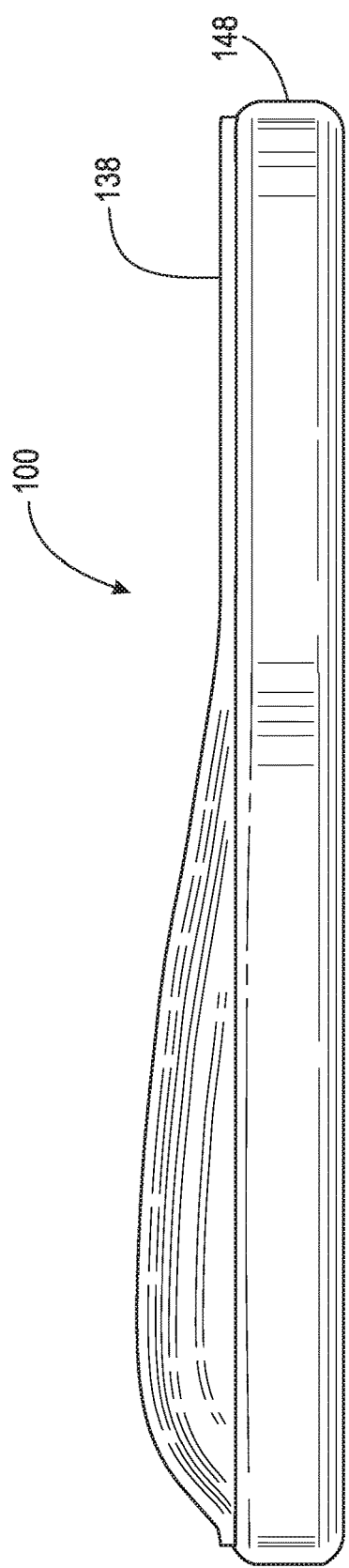
FIG. 7a is a left side elevational view of an assembly for the thermal treatment, moisture treatment, and/or medicated treatment of physical conditions as disclosed herein.
Figure 7B:
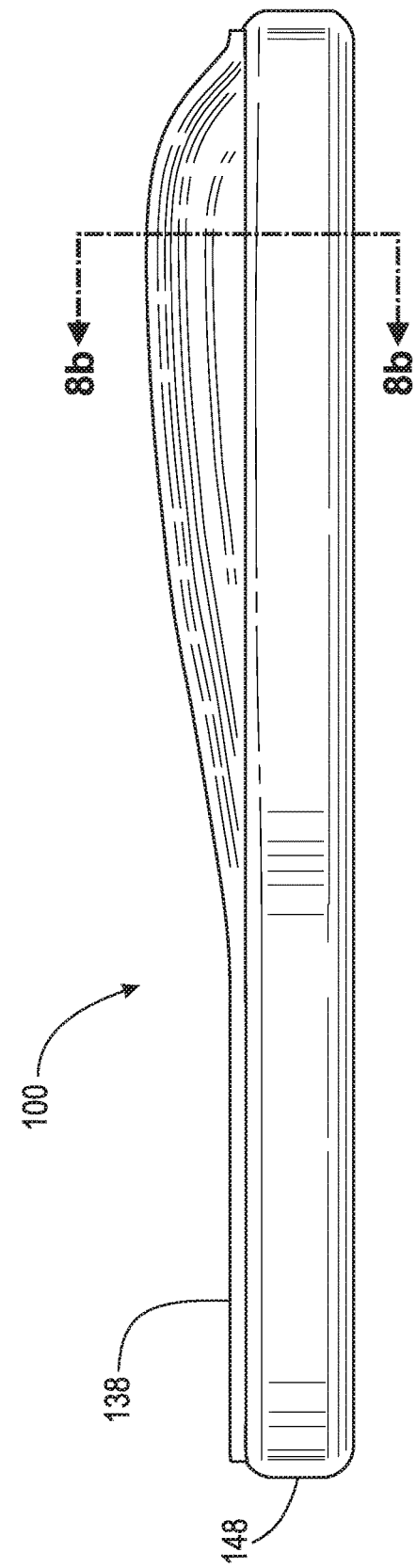
FIG. 7b is a right side elevational view of an assembly for the thermal treatment, moisture treatment, and/or medicated treatment of physical conditions as disclosed herein.

The following should be read in view of FIGS. 5-8b. FIG. 5 is an exploded perspective view of assembly 100. As illustrated in FIG. 5, assembly 100 further comprises medicament pad 138 having first surface 140 and second surface 142. First surface 140 of medicament pad 138 is intended to contact the various portions of the perineal area discussed supra and aid in recovery. Second surface 142 further comprises first fastening material 144 arranged to engage with sleeve 148 discussed infra. Medicament pad 138 can be soaked, sprayed, impregnated, saturated, or infused with a composition, which is discussed at length infra. First fastening material 144 is any material arranged to releasably secure medicament pad 138 to sleeve 148 such that medicament pad 138 does not slide, shift, or become separated in any way while assembly 100 is in use. Sleeve 148 and medicament pad 138 are preferably made from a non-woven fabric material. The non-woven fabric material for medicament pad 138 is suitable to accept a composition discussed infra; however, it should be appreciated that any suitable material that can accept and retain a composition could be used.

Assembly 100 further includes sleeve 148. Sleeve 148 has first surface 150, second surface 152, aperture 154, and cavity 156. First surface 150 of sleeve 148 further includes second fastening material 158 operatively arranged to engage with first fastening material 144 on second surface 142 of medicament pad 138. As a non-limiting example, first fastening material 144 could be hook or loop fastening material arranged to releasably secure with a respective hook or loop of second fastening material 158. Aperture 154 and cavity 156 are intended to receive and secure thermal pack 102, respectively. Thermal pack 102 can be inserted in and through aperture 154 until completely enclosed within cavity 156 of sleeve 148. Additionally, FIGS. 8a-8b show cross-sectional views of assembly 100 taken generally along line 8a-8a in FIG. 6a, and line 8b-8b in FIG. 7b, respectively. From these views, material 104 can be seen within thermal pack 102.

Figure 9:
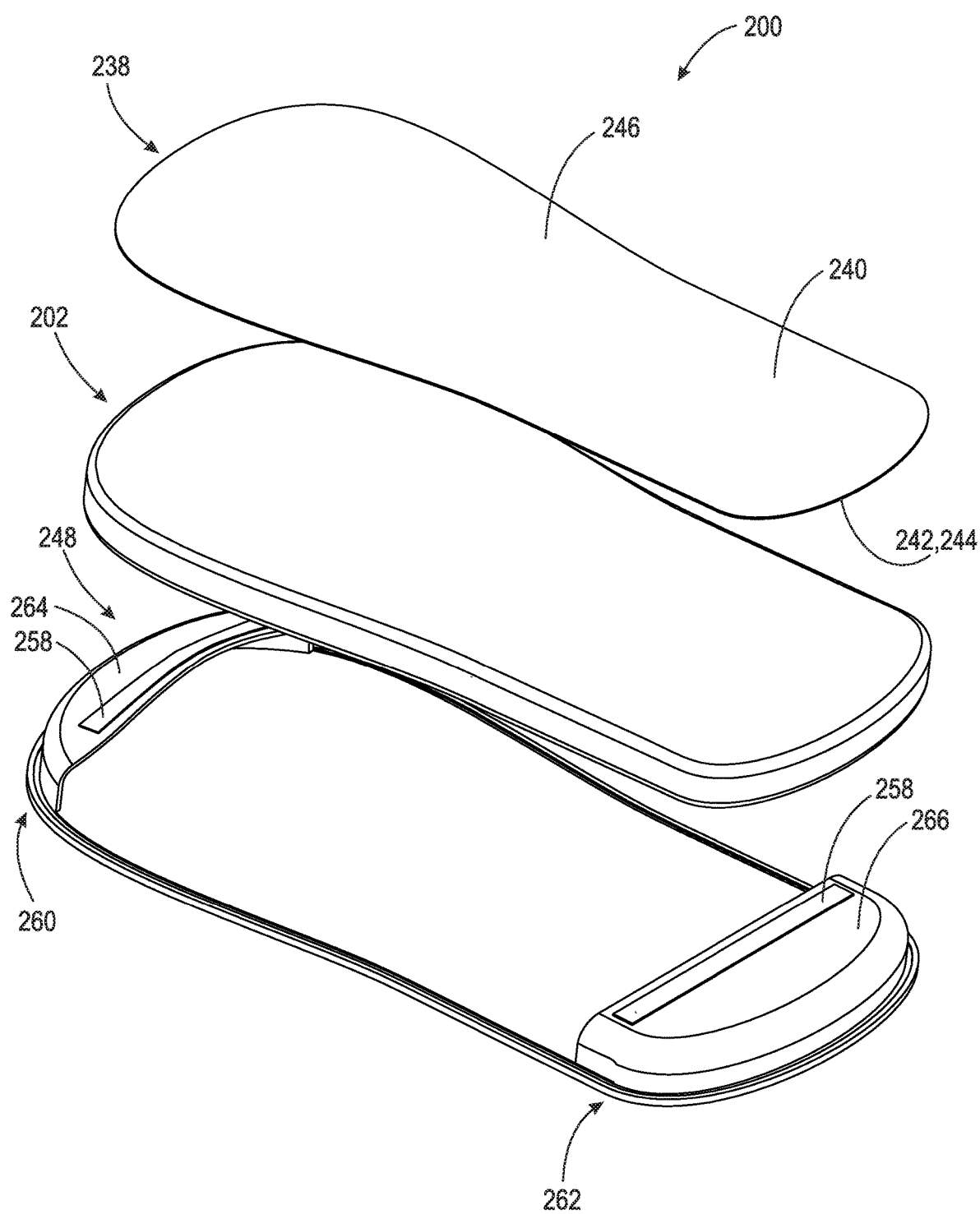
FIG. 9 is an exploded front perspective view of an assembly for the thermal treatment, moisture treatment, and/or medicated treatment of physical conditions as disclosed herein.
Figure 10:
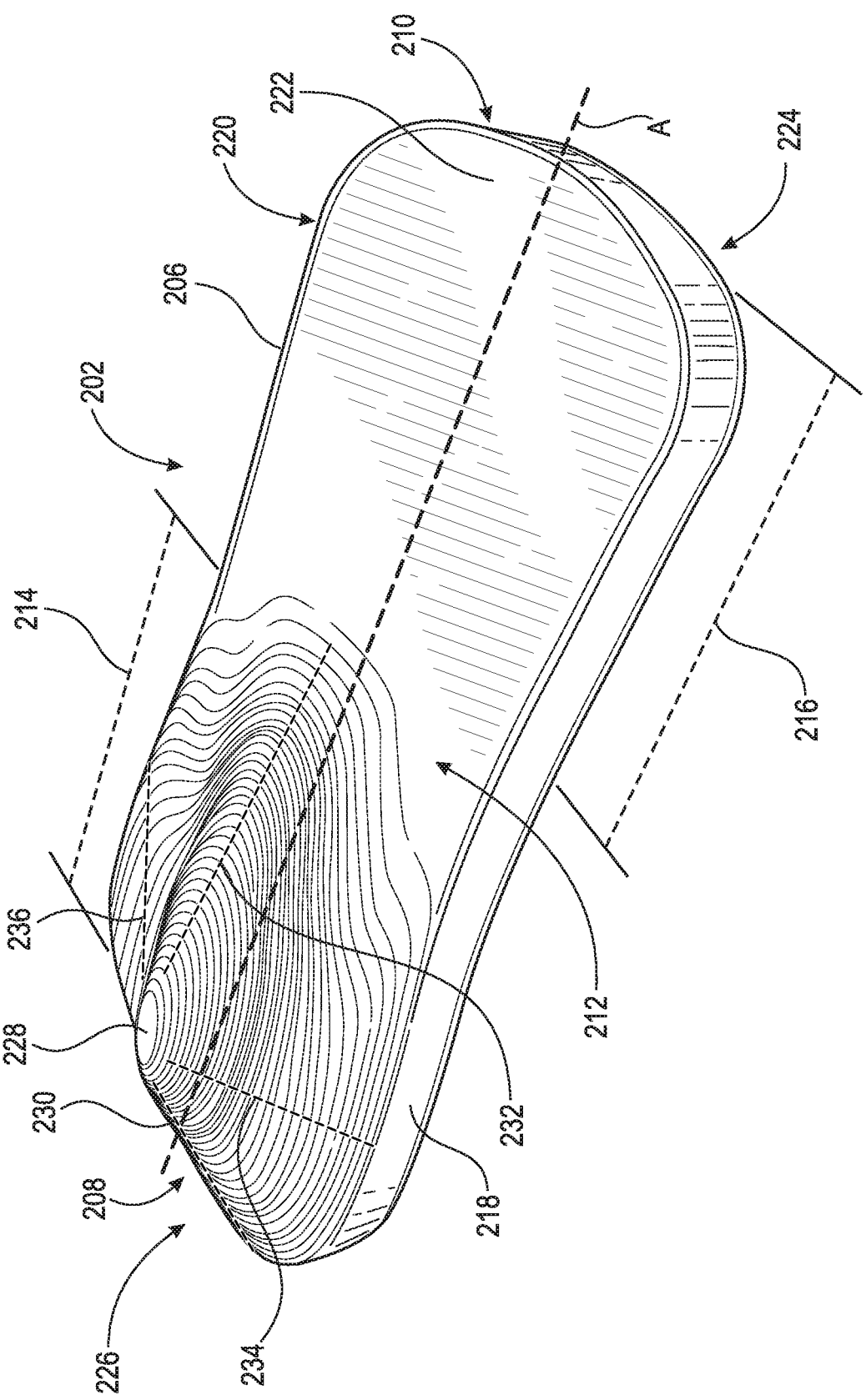
FIG. 10 is a front side perspective view of a device for the thermal treatment of physical conditions as disclosed herein.
Figure 11:
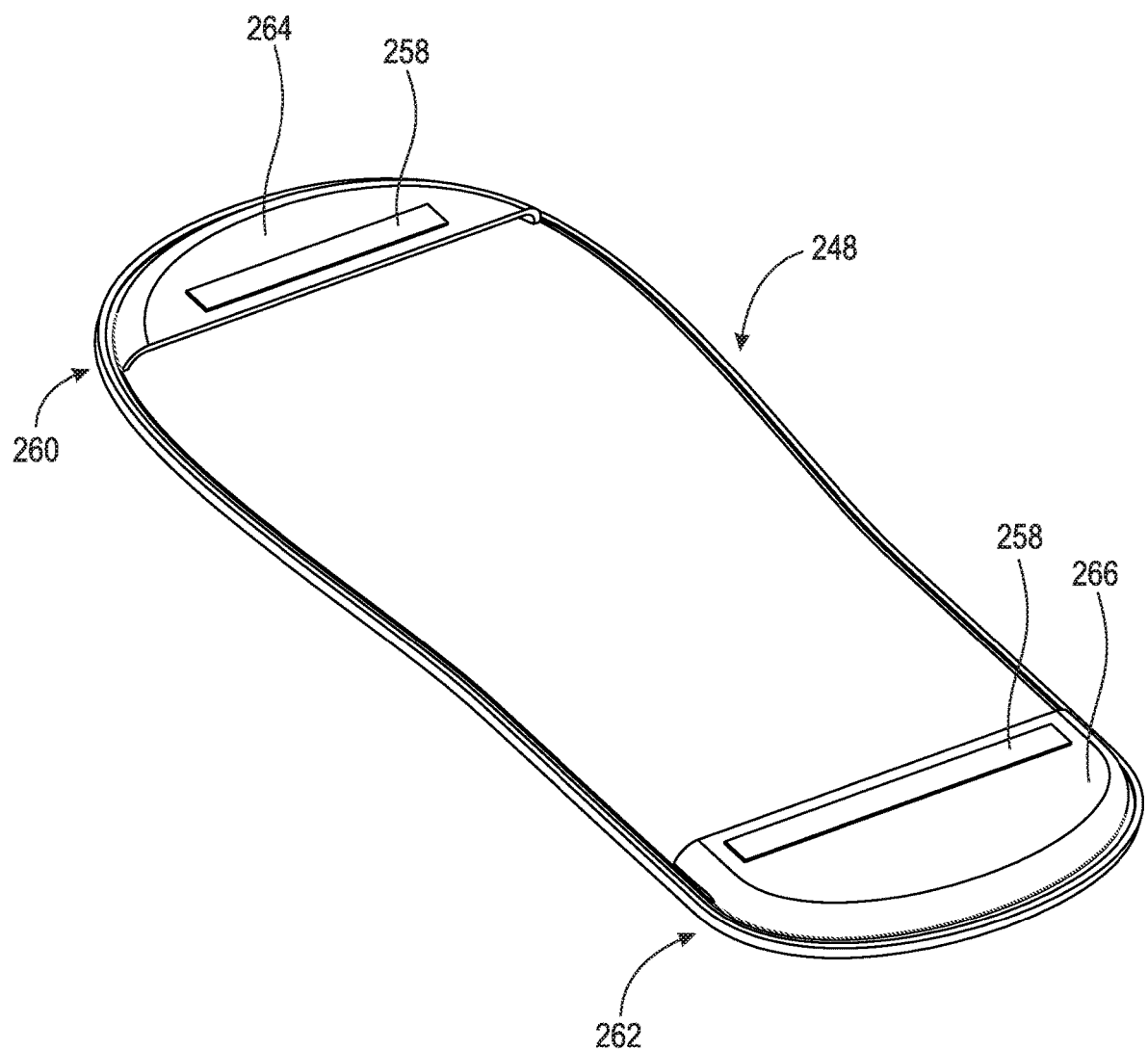
FIG. 11 is a front perspective view of a sleeve as used in an assembly for the thermal treatment, moisture treatment, and/or medicated treatment of physical conditions as disclosed herein.
Figure 14:
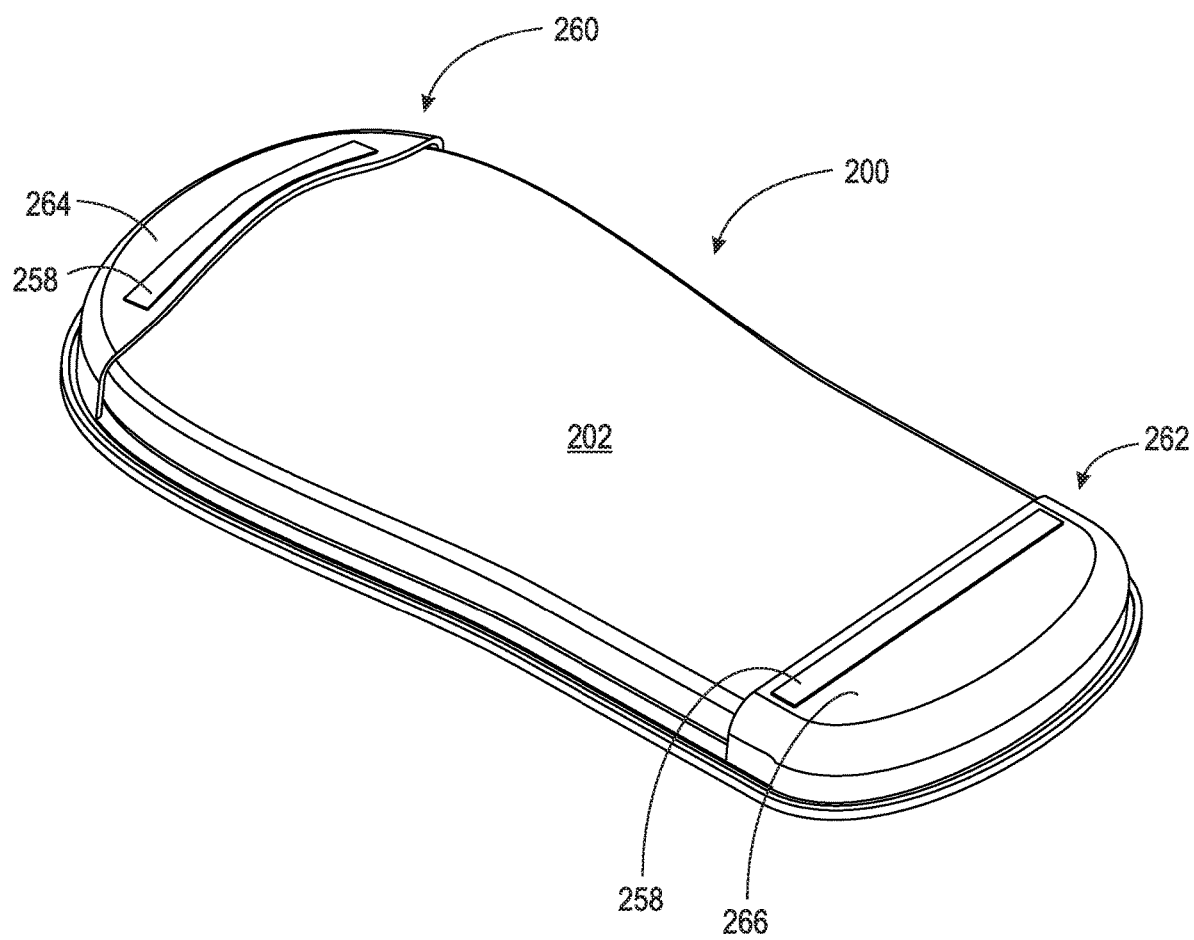
FIG. 14 is a front perspective view of an assembly for the thermal treatment, moisture treatment, and/or medicated treatment of physical conditions as disclosed herein.

The following should be read in view of FIGS. 9-14. FIGS. 9-14 illustrate another example embodiment of the invention disclosed herein. FIG. 9 illustrates assembly 200. Assembly 200 includes thermal pack 202 having body 206 which is substantially similar to thermal pack 102 discussed supra. Assembly 200 also includes medicament pad 238 having first surface 240 and second surface 242. Thermal pack 202 includes thermal material 204 (not shown) within body 206. Thermal material 204 can include but is not limited to materials such as thermally conductive silica gel, ceramic beads, glass beads, vinyl-based synthetic beads, sodium acetate, sodium polyacrylate, hydroxyethyl cellulose, paraffin, rice, flax seed, barley, corn, buckwheat, etc. Body 206 has first end 208, second end 210, middle 212, first portion 214, and second portion 216. First portion 214 is defined by the part of body 206 between middle 212 and first end 208. Second portion 216 is defined by the part of body 206 between middle 212 and second end 210. Body 206 further includes first side 218, second side 220, first face 222 and second face 224. First side 218 is substantially perpendicular to first face 222 and co-terminus with axis A. Second side 220 is substantially perpendicular to first face 222, co-terminus with axis A, and disposed opposite first side 218. On first face 222, and within the first portion 214, body 206 further includes first protrusion 226.

Protrusion 226 is defined by apex 228, first slope 230, second slope 232, third slope 234, and fourth slope 236. Apex 228 is the highest point on protrusion 228. First slope 230 is defined by a gradual height gradient with respect to first face 222 starting at apex 228 and terminating at the edge of first face 222 proximate first end 208. Second slope 232 is defined by a gradual height gradient with respect to first face 222 starting at apex 228 and terminating at the edge of first portion 214 proximate middle 212 of body 206. The height gradient of first slope 230 is substantially larger, i.e., steeper, than the height gradient of second slope 232. Third slope 234 is defined by a gradual height gradient with respect to first face 222 starting at apex 228 and terminating at the junction of first side 218 and first face 222. Fourth slope 236 is defined by a gradual height gradient with respect to first face 222 starting at apex 228 and terminating at the junction of second side 220 and first face 222. The height gradient of third slope 234 and fourth slope 236 are intended to be substantially similar, i.e., symmetrical; however, it should be appreciated that the height gradients of both third slope 234 and fourth slope 236 do not have to be equal. Additionally, the height gradient of third slope 234 and fourth slope 236, are intended to be larger, i.e., steeper than second slope 232 but smaller, i.e., less steep than first slope 230. The shape of protrusion 226, via slopes 230-234 is intended to be the anatomical negative of the human anus so as to provide user 10, when sitting on assembly 200, with heating/cooling therapy to the entire perineal area including for example, the anus.

First surface 240 of medicament pad 238 is intended to contact the various portions of the perineal area discussed supra and aid in recovery. Second surface 242 further comprises first fastening material 244 arranged to engage with sleeve 248 discussed infra. Medicament pad 238 can be soaked, sprayed, impregnated, saturated, or infused with composition 246, which is discussed at length infra. First fastening material 244 is any material arranged to releasably secure medicament pad 238 to sleeve 248 such that medicament pad 238 does not slide, shift, or become separated in any way while the assembly is in use. Sleeve 248 and medicament pad 238 are preferably made from a non-woven fabric material. The non-woven fabric material for medicament pad 238 is suitable to accept composition 246 discussed infra; however, it should be appreciated that any suitable material that can accept and retain composition 246 could be used.

Assembly 200 further includes sleeve 248. Sleeve 248 has first partial-enclosure 260, and second partial-enclosure 262. First partial-enclosure 260 of sleeve 248 further includes second surface 264 having second fastening material 258 operatively arranged to engage with first fastening material 244 on second surface 242 of medicament pad 238. Second partial-enclosure 262 of sleeve 248 includes third surface 266 having second fastening material 258 operatively arranged to engage with first fastening material 244 of second surface 242 of medicament pad 238. As a non-limiting example, first fastening material 244 could be hook or loop fastening material arranged to releasably secure with a respective hook or loop of second fastening material 258. First end 208 of thermal pack 202 can be inserted within and secured by first partial-enclosure 260 and second end 210 of thermal pack 202 can be inserted within and secured by second partial-enclosure 262.

Figure 15:
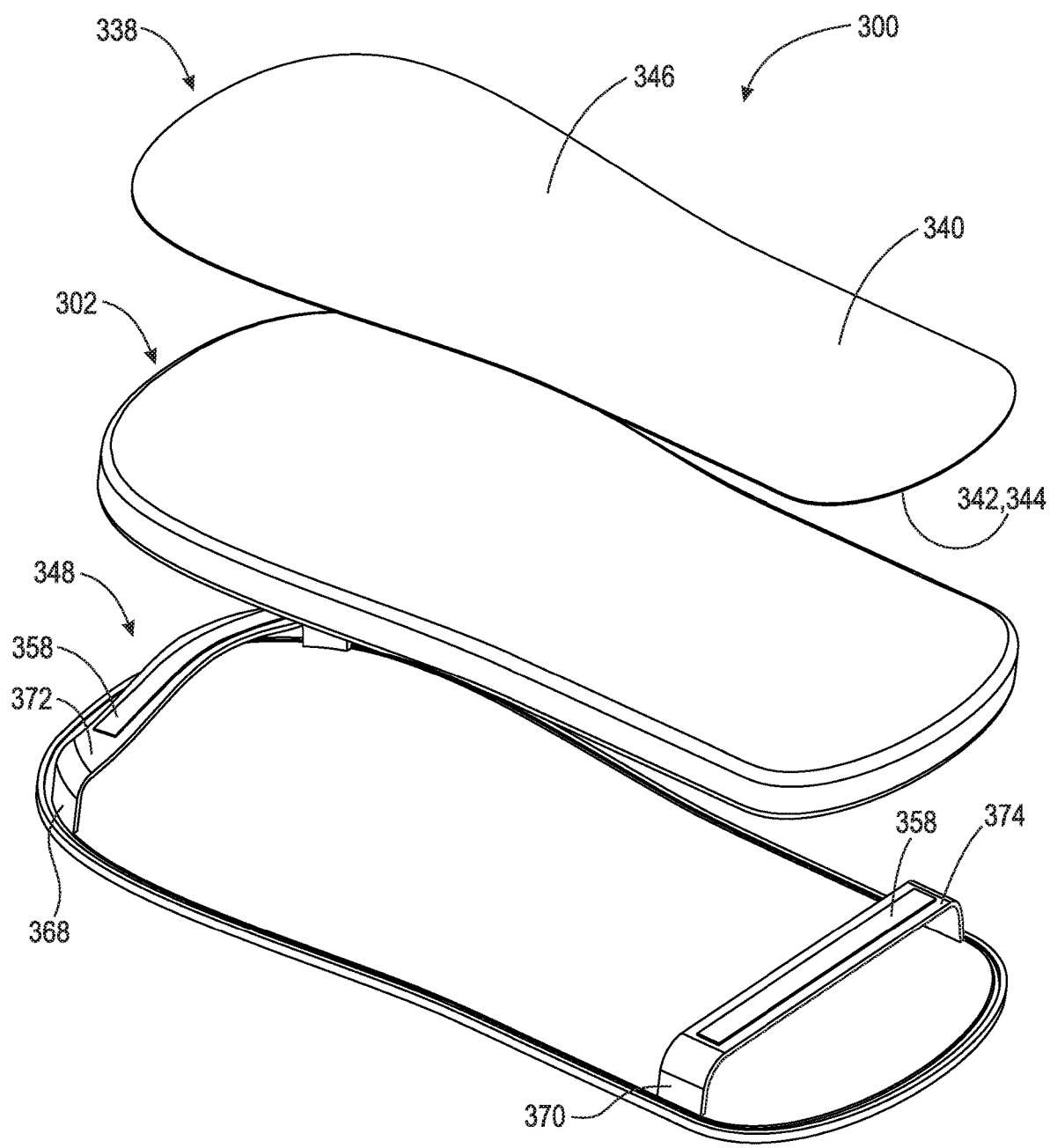
FIG. 15 is an exploded front perspective view of an assembly for the thermal treatment, moisture treatment, and/or medicated treatment of physical conditions as disclosed herein.
Figure 16:
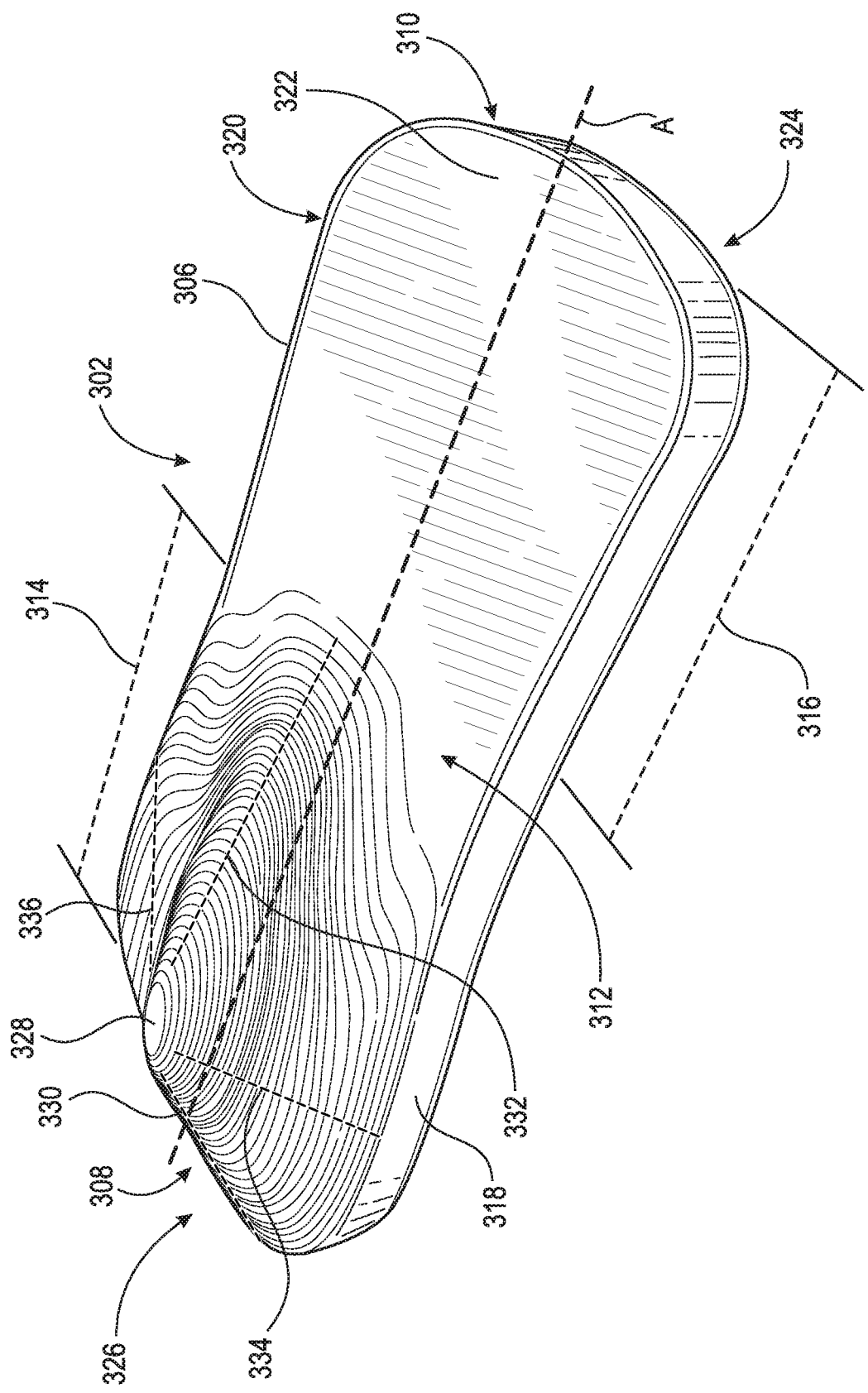
FIG. 16 is a front side perspective view of a device for the thermal treatment of physical conditions as disclosed herein.
Figure 17:
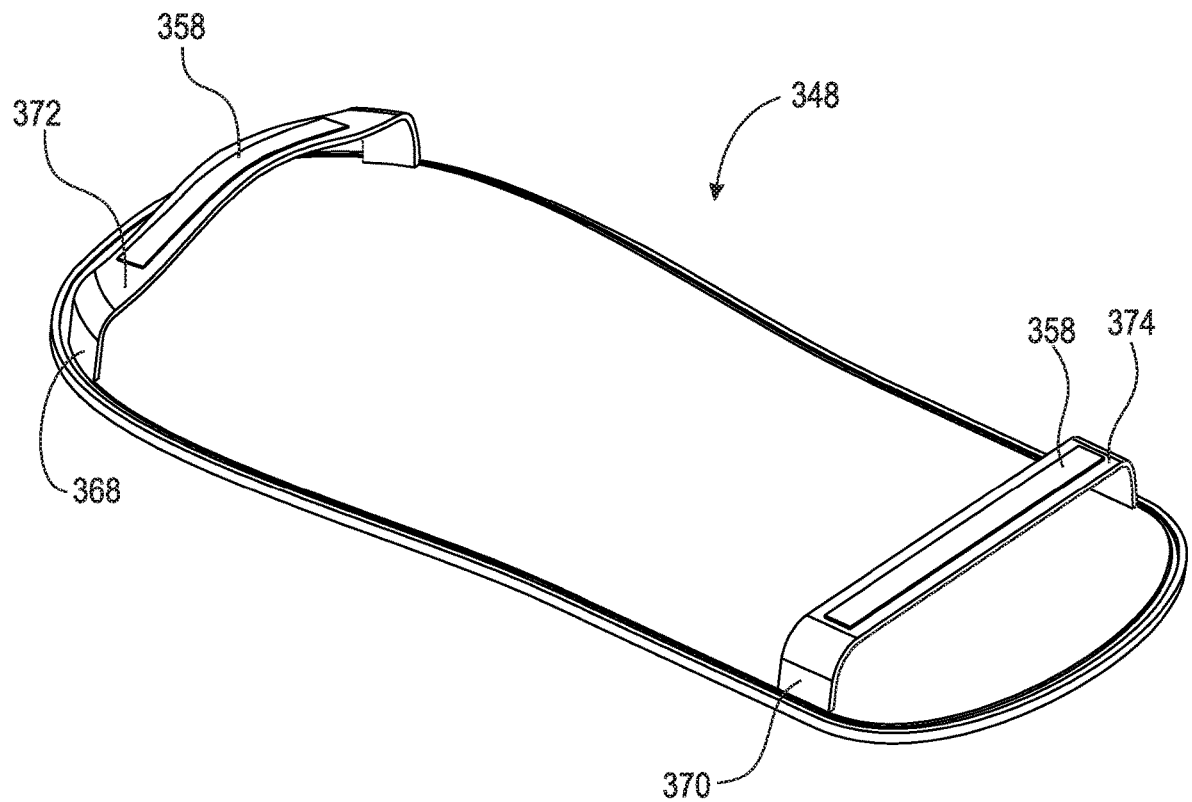
FIG. 17 is a front perspective view of a sleeve as used in an assembly for the thermal treatment, moisture treatment, and/or medicated treatment of physical conditions as disclosed herein.
Figure 18:
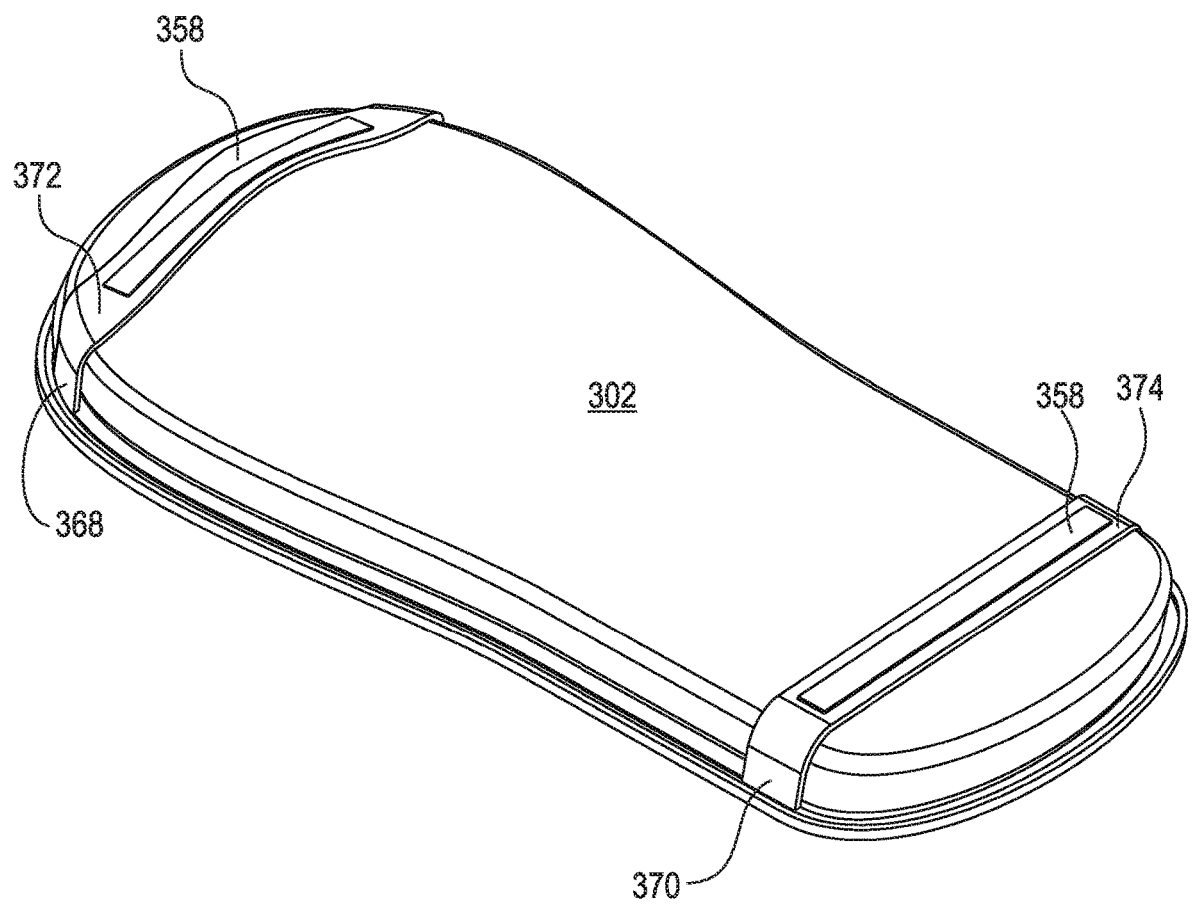
FIG. 18 is a front perspective view of an assembly for the thermal treatment, moisture treatment, and/or medicated treatment of physical conditions as disclosed herein.

The following should be read in view of FIGS. 15-18. FIG. 15 illustrates another example embodiment of the invention disclosed herein. FIG. 15 illustrates assembly 300. Assembly 300 includes thermal pack 302 having body 306, which is substantially similar to thermal packs 102 and 202 discussed supra. Assembly 300 further includes medicament pad 338 having first surface 340 and second surface 342. Thermal pack 302 includes thermal material 304 (not shown) within body 306. Thermal material 304 can include but is not limited to materials such as thermally conductive silica gel, ceramic beads, glass beads, vinyl-based synthetic beads, sodium acetate, sodium polyacrylate, hydroxyethyl cellulose, paraffin, rice, flax seed, barley, corn, buckwheat, etc. Body 306 has first end 308, second end 310, middle 312, first portion 314, and second portion 316. First portion 314 is defined by the part of body 306 between middle 312 and first end 308. Second portion 316 is defined by the part of body 306 between middle 312 and second end 310. Body 306 further includes first side 318, second side 320, first face 322 and second face 324. First side 318 is substantially perpendicular to first face 322 and co-terminus with axis A. Second side 320 is substantially perpendicular to first face 322, co-terminus with axis A, and disposed opposite first side 318. On first face 322, and within the first portion 314, body 306 further includes first protrusion 326.

Protrusion 326 is defined by apex 328, first slope 330, second slope 332, third slope 334, and fourth slope 336. Apex 328 is the highest point on protrusion 328. First slope 330 is defined by a gradual height gradient with respect to first face 322 starting at apex 328 and terminating at the edge of first face 322 proximate first end 308. Second slope 332 is defined by a gradual height gradient with respect to first face 322 starting at apex 328 and terminating at the edge of first portion 314 proximate middle 312 of body 306. The height gradient of first slope 330 is substantially larger, i.e., steeper, than the height gradient of second slope 332. Third slope 334 is defined by a gradual height gradient with respect to first face 322 starting at apex 328 and terminating at the junction of first side 318 and first face 322. Fourth slope 336 is defined by a gradual height gradient with respect to first face 322 starting at apex 328 and terminating at the junction of second side 320 and first face 322. The height gradient of third slope 334 and fourth slope 336 are intended to be substantially similar, i.e., symmetrical; however, it should be appreciated that the height gradients of both third slope 334 and fourth slope 336 do not have to be equal. Additionally, the height gradient of third slope 334 and fourth slope 336, are intended to be larger, i.e., steeper than second slope 332 but smaller, i.e., less steep than first slope 330. The shape of protrusion 326, via slopes 330-334 is intended to be the anatomical negative of the human anus so as to provide user 10, when sitting on assembly 300, with heating/cooling therapy to the entire perineal area including for example, the anus.

First surface 340 of medicament pad 338 is intended to contact the various portions of the perineal area discussed supra and aid in recovery. Second surface 342 further comprises first fastening material 344 arranged to engage with sleeve 348 discussed infra. Medicament pad 338 can be soaked, sprayed, impregnated, saturated, or infused with composition 346, which is discussed at length infra. First fastening material 344 is any material arranged to releasably secure medicament pad 338 to sleeve 348 such that medicament pad 338 does not slide, shift, or become separated in any way while the assembly is in use. Sleeve 348 and medicament pad 338 are preferably made from a non-woven fabric material. The non-woven fabric material for medicament pad 338 is suitable to accept composition 346 discussed infra; however, it should be appreciated that any suitable material that can accept and retain composition 346 could be used.

Assembly 300 further includes sleeve 348. Sleeve 348 has first strap 368, and second strap 370. First strap 368 of sleeve 348 further includes second surface 372 having second fastening material 358 operatively arranged to engage with first fastening material 344 on second surface 342 of medicament pad 338. Second strap 370 of sleeve 348 includes third surface 374 having second fastening material 358 operatively arranged to engage with first fastening material 344 of second surface 342 of medicament pad 338. As a non-limiting example, first fastening material 344 could be hook or loop fastening material arranged to releasably secure with a respective hook or loop of second fastening material 358. First end 308 of thermal pack 302 can be inserted within and secured by first strap 368 and second end 310 of thermal pack 302 can be inserted within and secured by second strap 370.

Figure 19A:
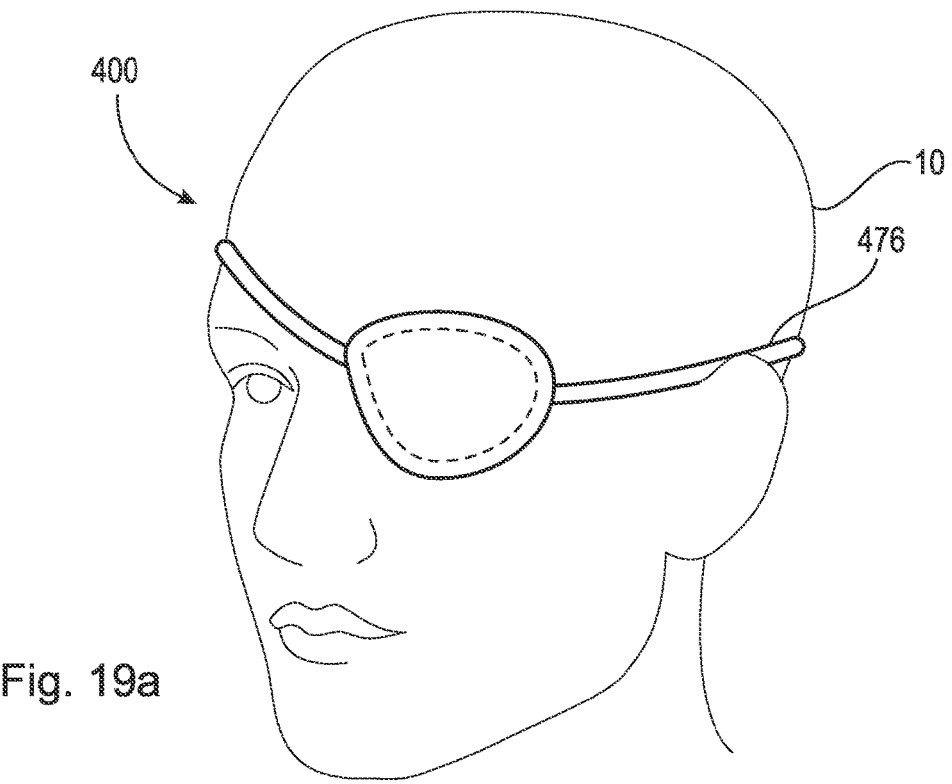
FIG. 19a is a front perspective view of an assembly for the thermal treatment, moisture treatment, and/or medicated treatment of physical conditions in context as disclosed herein.
Figure 19B:
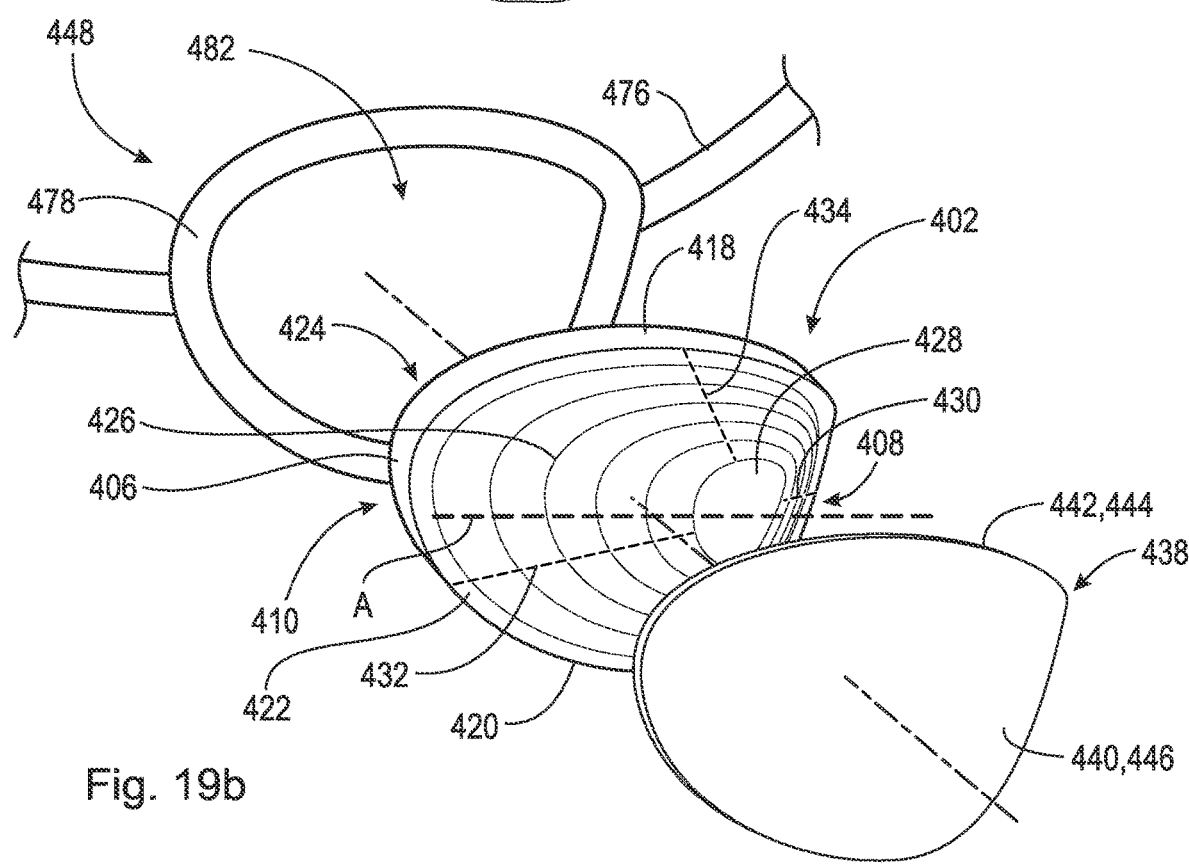
FIG. 19b is an exploded rear perspective view of an assembly for the thermal treatment, moisture treatment, and/or medicated treatment of physical conditions as disclosed herein.

The following should be read in view of FIGS. 19a-20b. FIGS. 19a-20b illustrate another example embodiment of the invention disclosed herein. FIG. 19a illustrates assembly 400. Assembly 400 includes thermal pack 402 having body 406. Assembly 400 also includes medicament pad 438 having first surface 440 and second surface 442. Thermal pack 402 includes a thermal material (not shown) within body 406. The thermal material can include but is not limited to materials such as thermally conductive silica gel, ceramic beads, glass beads, vinyl-based synthetic beads, sodium acetate, sodium polyacrylate, hydroxyethyl cellulose, paraffin, rice, flax seed, barley, corn, buckwheat, etc. Body 406 has first end 408 and second end 410. Body 406 further includes first side 418, second side 420, first face 422 and second face 424. First side 418 is substantially perpendicular to first face 422 and co-terminus with axis A. Second side 420 is substantially perpendicular to first face 422, co-terminus with axis A, and disposed opposite first side 418. On first face 422, body 406 may further include, but does not need to include first protrusion 426. In a preferred embodiment there is no protrusion on first face 422.

Protrusion 426 is defined by apex 428, first slope 430, second slope 432, third slope 434, and fourth slope 436. Apex 428 is the highest point on protrusion 426. First slope 430 is defined by a gradual height gradient with respect to first face 422 starting at apex 428 and terminating at the edge of first face 422 proximate first end 408. Second slope 432 is defined by a gradual height gradient with respect to first face 422 starting at apex 428 and terminating at the junction of second end 410 and first face 422 of body 406. The height gradient of first slope 430 is larger, i.e., steeper, than the height gradient of second slope 432. Third slope 434 is defined by a gradual height gradient with respect to first face 422 starting at apex 428 and terminating at the junction of first side 418 and first face 422. Fourth slope 436 is defined by a gradual height gradient with respect to first face 422 starting at apex 428 and terminating at the junction of second side 420 and first face 422. The height gradient of third slope 434 and fourth slope 436 are intended to be substantially similar, i.e., symmetrical; however, it should be appreciated that the height gradients of both third slope 434 and fourth slope 436 do not have to be equal. Additionally, the height gradient of third slope 434 and fourth slope 436, are intended to be larger, i.e., steeper than second slope 432 but smaller, i.e., less steep than first slope 430. The shape of protrusion 426, via slopes 430, 432, 434, and 436 is intended to be the anatomical negative of the human eye socket so as to provide user 10, while using assembly 300, with heating/cooling therapy to the entire eye socket area.

First surface 440 of medicament pad 438 is intended to contact the eye socket and aid in recovery. Second surface 442 further comprises first fastening material 444 arranged to engage with sleeve 448 discussed infra. Medicament pad 438 can be soaked, sprayed, impregnated, saturated, or infused with composition 446, which is discussed at length infra. First fastening material 444 is any material arranged to releasably secure medicament pad 438 to sleeve 448 such that medicament pad 438 does not slide, shift, or become separated in any way while the assembly is in use. Sleeve 448 and medicament pad 438 are preferably made from a non-woven fabric material. The non-woven fabric material for medicament pad 438 is suitable to accept composition 446 discussed infra; however, it should be appreciated that any suitable material that can accept and retain composition 446 could be used.

Assembly 400 further includes sleeve 448. Sleeve 448 has head strap 476, and retaining rim 478. Head strap 476 is operatively arranged to surround and secure assembly 400 to the head of user 10. Retaining rim 478 is partially deformable such that thermal pack 402 can sit within and be secured by retaining rim 478. Retaining rim 478 further comprises first surface 480 which includes first fastening material 444 arranged to engage with second fastening material 458 on second surface 442 of medicament pad 438. As a non-limiting example, first fastening material 444 could be hook or loop fastening material arranged to releasably secure with a respective hook or loop of second fastening material 458. Thermal pack 402 can be inserted within and secured within apertures 482 or 484 by retaining rim 478 while in use by user 10.

Figure 20A:
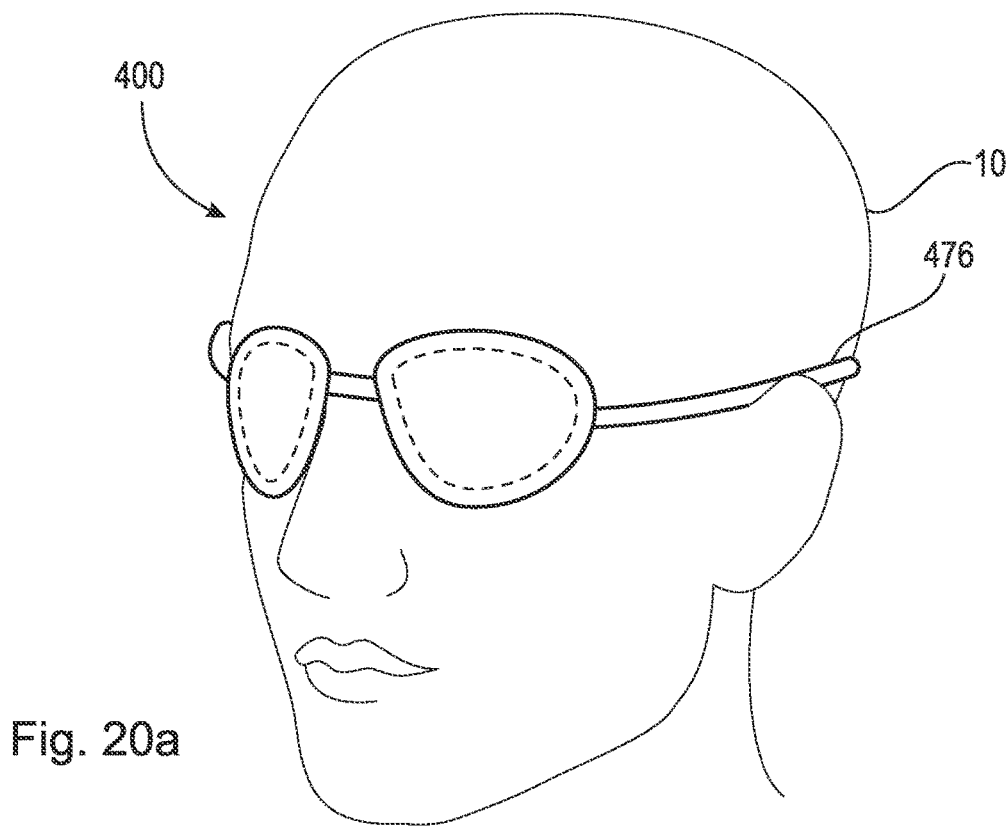
FIG. 20a is a front perspective view of an assembly for the thermal treatment, moisture treatment, and/or medicated treatment of physical conditions in context as disclosed herein; and, FIG. 20b is an exploded rear perspective view of an assembly for the thermal treatment, moisture treatment, and/or medicated treatment of physical conditions as disclosed herein.
Figure 20B:
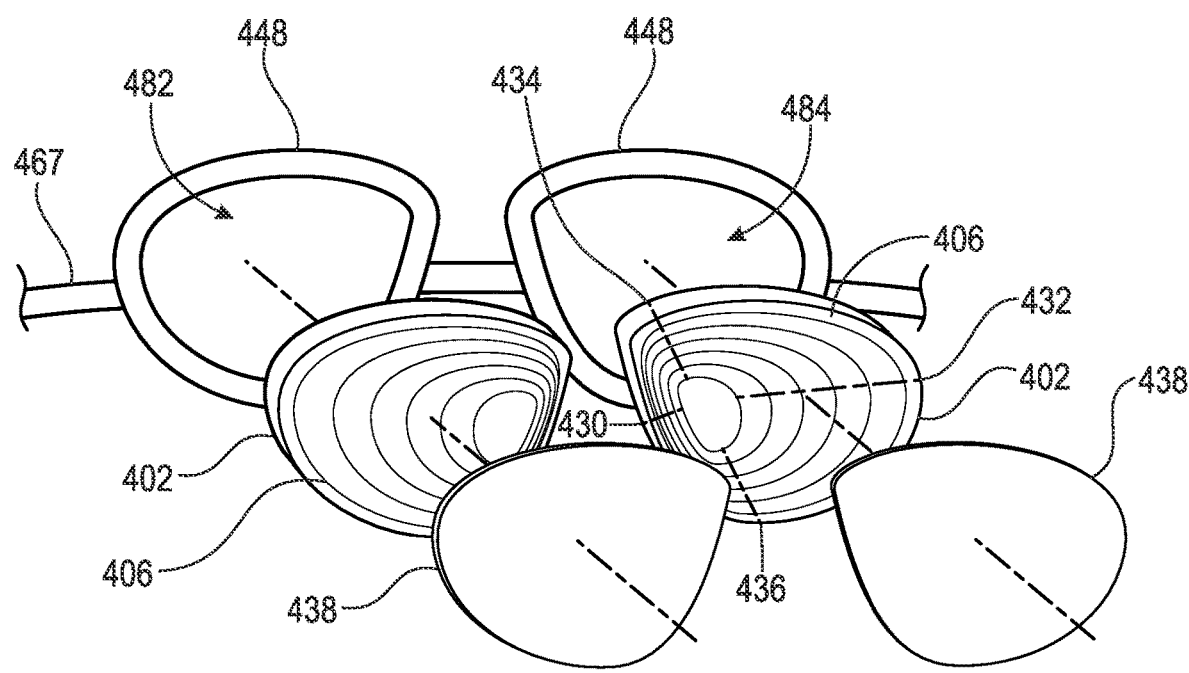

As shown in FIGS. 20a-20b, it should be appreciated that assembly 400 can be duplicated into a mask type arrangement having two instances of sleeve 448, thermal pack 402, and medicament pad 438 connected by a single head strap 476. It should be appreciated that in the mask embodiment shown in FIGS. 20a-20b, the second instance of sleeve 448, thermal pack 402, and medicament pad 438 is rotated 180 degrees such that the apex 428 of protrusion 426 conforms to the symmetrical nature of both eye sockets of user 10 about the nose. Although not shown, it should also be appreciated that the two sleeves 448 could be combined into a single sleeve, similar to a sleeping mask, and contain two cavities to receive the thermal packs 402.

As discussed supra, medicament pads (138, 238, 338, 438) can be soaked, sprayed, impregnated, saturated, or infused with compositions (246, 346, 446). These compositions can take the form and/or concentrations of any of the following example embodiments.

A first example embodiment of the compositions discussed supra, includes a 10-50% concentration of Witch hazel; 10-40% concentration of Water; 1-15% concentration of Glycerin; 1-10% concentration of Alcohol; 0.1-5% concentration of Iodopropynyl Butylcarbamate; 0.1-5% concentration of Benzalkonium Chloride; 0.1-5% concentration of 2-Bromo-2nitropropane-1; 0.1-8% concentration of 3-diol; 0.1-10% concentration of Citric Acid; 0.1-2% concentration of Sodium Acid; and 1-10% concentration of *Chamomilla recutita* (Matricaria) Extract.

A second example embodiment of the compositions discussed supra, includes a 12.5-25% concentration of Lanolin; 12.5-25% concentration of Coco butter; 2-10% concentration of Propylene glycol; 1-10% concentration of *Chamomilla recutita* (Matricaria) Extract; 0.1-5% concentration of Benzalkonium chloride; 0.2-8% concentration of 2-bromo-2-nitropropane-1,3-diol; 2-10% concentration of Disodium cocoamphoacetate OR coconut oil; 0.1-10% concertation of Citric acid; and 10-40% concentration of Purified water.

A third example embodiment of the compositions discussed supra, includes a 50% concentration of Witch hazel; 10-40% concentration of Water; 1-15% concentration of Glycerin; 1-10% concentration of Alcohol; 8-30% concentration of Propylene glycol; 0.1-10% concentration of Sodium citrate; 5-15% concentration of Diazolidinyl urea; 0.1-10% concentration of Citric acid; 0.1-2% concentration of Methyl paraben; and, 0.1-2% concentration of Propyl paraben.

A fourth example embodiment of the compositions discussed supra, includes a 50% concentration of Witch hazel; 1-10% concentration of Aloe barbadensis leaf juice; 0.1-10% concentration of Anhydrous citric acid; 0.1-5% concentration of Capryl/capramidopropyl betaine; 5-15% concentration of Diazolidinyl urea; 1-15% concentration of Glycerin; 0.1-2% concentration of Methyl paraben; 8-30% concentration of Propylene glycol; 0.1-2% concentration of Propyl paraben; 10-40% concentration of Purified water; and, 0.1-10% concentration of Sodium citrate.

A fifth example embodiment of the compositions discussed supra, includes a 2-5% concentration of Lidocaine; 20-50% concentration of Cocoa Butter and/or Lanolin; 10-50% concentration of Witch Hazel; 10-40% concentration of Water; 1-15% concentration of Glycerin; 1-10% concentration of Alcohol; 1-10% concentration of Iodopropynyl Butylcarbamate; 0.1-5% concentration of Benzalkonium Chloride; 0.1-5% concentration of 2-Bromo-2nitropropane-1; 1-8% concentration of 3-diol; 0.1-10% concentration of Citric Acid; 0.1-2% concentration of Sodium Acid; and, 1-10% concentration of *Chamomilla recutita* (Matricaria) Extract.

A sixth example embodiment of the compositions discussed supra, includes a 5-20% concentration of Benzocaine; 20-50% concentration of Cocoa Butter and/or Lanolin; 10-50% concentration of Witch Hazel; 10-40% concentration of Water; 1-15% concentration of Glycerin; 1-10% concentration of Alcohol; 0.1-5% concentration of Iodopropynyl Butylcarbamate; 0.1-5% concentration of Benzalkonium Chloride; 0.1-5% concentration of 2-Bromo-2nitropropane-1; 0.1-8% concentration of 3-diol; 0.1-10% concentration of Citric Acid; 0.1-2% concentration of Sodium Acid; and, 1-10% concentration of *Chamomilla recutita* (Matricaria) Extract.

A seventh example embodiment of the compositions discussed supra, includes a 0.1-3% concentration of Camphor OR 1-5% concentration of Juniper tar; 20-50% concentration of Cocoa Butter and/or Lanolin; 10-50% concentration of Witch Hazel; 10-40% concentration of Water; 1-15% concentration of Glycerin; 1-10% concentration of Alcohol 1-10%; 0.1-5% concentration of Iodopropynyl Butylcarbamate; 0.1-5% concentration of Benzalkonium Chloride; 0.1-5% concentration of 2-Bromo-2nitropropane-1; 0.1-8% concentration of 3-diol; 0.1-10% Citric Acid; 0.1-2% Sodium Acid; and, 1-10% concentration of *Chamomilla recutita* (Matricaria) Extract.

An eighth example embodiment of the compositions discussed supra, includes a 1-10% concentration of Epson Salt; 10-50% concentration of Witch Hazel; 12-30% concentration of Cocoa butter; 2-10% concentration of Propylene glycol; 1-10% concentration of *Chamomilla recutita* (Matricaria) Extract; 0.1-5% concentration of Benzalkonium chloride; 0.2-8% concentration of 2-bromo-2-nitropropane-1, 3-diol; 2-10% concentration of Disodium cocoamphoacetate or Coconut oil; 0.1-10% concentration of Citric acid; and 10-40% concentration of Purified water.

A ninth example embodiment of the compositions discussed supra, includes a 1-10% concentration of Epson Salt; 50% concentration of Cocoa butter; 2-10% concentration of Propylene glycol; 1-10% concentration of *Chamomilla recutita* (Matricaria) Extract; 0.1-5% concentration of Benzalkonium chloride; 0.2-8% concentration of 2-bromo-2-nitropropane-1, 3-diol; 2-10% concentration of Disodium cocoamphoacetate or Coconut oil; 0.1-10% concentration of Citric acid; and, 10-40% concentration of Purified water.

A tenth example embodiment of the compositions discussed supra, includes 100% Purified water or 100% distilled water, or 100% non-distilled water.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

LIST OF REFERENCE NUMERALS

A Axis
10 User
20 Chair
30 Perineal area
100 Assembly
102 Thermal pack
104 Thermal material
106 Body
108 First end of body
110 Second end of body
112 Middle of body
114 First portion of body
116 Second portion of body
118 First side of body
120 Second side of body
122 First face
124 Second face
126 First protrusion
128 Apex
130 First slope of protrusion
132 Second slope of protrusion
134 Third slope of protrusion
136 Fourth slope of protrusion
138 Medicament pad
140 First surface of medicament layer
142 Second surface of medicament layer
144 First fastening material
148 Sleeve
150 First surface of sleeve
152 Second surface of sleeve
154 Aperture
156 Cavity
158 Second fastening material
200 Assembly
202 Thermal pack
204 Thermal material
206 Body
208 First end of body
210 Second end of body
212 Middle of body
214 First portion of body
216 Second portion of body
218 First side of body
220 Second side of body
222 First face
224 Second face
226 First protrusion
228 Apex
230 First slope of protrusion
232 Second slope of protrusion
234 Third slope of protrusion
236 Fourth slope of protrusion
238 Medicament pad
240 First surface of medicament layer
242 Second surface of medicament layer
244 First fastening material
246 Composition
248 Sleeve
258 Second fastening material
260 First partial-enclosure
262 Second partial-enclosure
264 Surface of first partial-enclosure (second surface)
266 Surface of Second partial-enclosure (third surface)
300 Assembly
302 Thermal pack
304 Thermal material
306 Body
308 First end of body
310 Second end of body
312 Middle of body
314 First portion of body
316 Second portion of body
318 First side of body
320 Second side of body
322 First face
324 Second face
326 First protrusion
328 Apex
330 First slope of protrusion
332 Second slope of protrusion
334 Third slope of protrusion
336 Fourth slope of protrusion
338 Medicament pad
340 First surface of medicament layer
342 Second surface of medicament layer
344 First fastening material
346 Composition
348 Sleeve
358 Second fastening material
368 First strap
370 Second strap
372 Surface of first strap
374 Surface of second strap
400 Assembly
402 Thermal pack 406 Body
408 First end of body
410 Second end of body
412 Middle of body
414 First portion of body
416 Second portion of body
418 First side of body
420 Second side of body
422 First face
424 Second face
426 First protrusion
428 Apex
430 First slope of protrusion
432 Second slope of protrusion
434 Third slope of protrusion
436 Fourth slope of protrusion
438 Medicament pad
440 First surface of medicament layer
442 Second surface of medicament layer
444 First fastening material
446 Composition
448 Sleeve
458 Second fastening material
476 Head strap
478 retaining rim
480 First surface of retaining rim
482 First aperture
484 Second aperture

What is claimed is:

1. A thermal pack for the thermal treatment of physical conditions, comprising:
a body, said body being substantially symmetrical about an imaginary longitudinal centerline, the body having a length L, said body comprising:
a chamber containing thermal material;
a first end;
a second end;
a middle, located substantially midway between said first end and said second end;
a first portion arranged between the first end and the middle;
a second portion arranged between the second end and the middle;
a first face, the first face having a first surface;
a second face, the second face having a second surface, the second surface being substantially planar;
a first side, generally perpendicular to and joining said first and second faces, said first side co-terminus with said imaginary longitudinal centerline;
a second side, generally perpendicular to and joining said first and second faces, said second side opposite said first side, and co-terminus with said imaginary longitudinal centerline, said first side and said second side are integrally connected to form a side wall, said side wall having a height defined by the distance between said first face and said second face, wherein said thermal material in said chamber abuts said first and second sides; and,
a first protrusion extending upwardly from the first surface of the first face and within the first portion, said protrusion having a length which is no greater than 70% of said length L of said body, said protrusion comprised of entirely non-planar surfaces, wherein the first protrusion further comprises an apex, wherein said apex is located proximate to said first end.

2. The thermal pack for the thermal treatment of physical conditions of claim 1 wherein the first protrusion further comprises a first slope operatively arranged between the first end of the body and the apex.

3. The thermal pack for the thermal treatment of physical conditions of claim 2 wherein the first protrusion further comprises a second slope operatively arranged between the apex and the second portion.

4. The thermal pack for the thermal treatment of physical conditions of claim 3 wherein the first protrusion further comprises a third slope and a fourth slope, the third slope operatively arranged between the apex and the first side and the fourth slope operatively arranged between the apex and the second side.

5. The thermal pack recited in claim 4 wherein said first slope is steeper than said second slope.

6. The thermal pack recited in claim 4 wherein said third slope and said fourth slope have substantially similar gradients.

7. The thermal pack recited in claim 6 wherein said third slope is steeper than said second slope.

8. The thermal pack recited in claim 6 wherein said fourth slope is steeper than said second slope.

9. An assembly for the thermal treatment, moisture treatment, and/or medicated treatment of physical conditions, comprising:
a first thermal pack having a body;
a sleeve operatively arranged to receive the first thermal pack, the sleeve having a first surface; and,
a medicament pad arranged to be removably secured to the first surface of the sleeve;
wherein the medicament pad comprises a chemical composition, the chemical composition having a concentration of about 10-40% Water; 1-15% Glycerin; 1-10% Alcohol; 0.1-5% Iodopropynyl Butylcarbamate; 0.1-5% Benzalkonium Chloride; 0.1-5% 2-Bromo-2nitropropane-1; 0.1-8% 3-diol; 0.1-10% Citric Acid; 0.1-2% Sodium Acetate; and a 1-10% *Chamomilla recutita* (Matricaria) Extract.

10. An assembly for the thermal treatment, moisture treatment, and/or medicated treatment of physical conditions, comprising:
a first thermal pack having a body;
a sleeve operatively arranged to receive the first thermal pack, the sleeve having a first surface; and,
a medicament pad arranged to be removably secured to the first surface of the sleeve wherein the chemical composition of the medicament pad comprises: a 12.5-25% concentration of Lanolin; 12.5-25% concentration of Coco butter; 2-10% concentration of Propylene glycol; 1-10% concentration of *Chamomilla recutita* (Matricaria) Extract; 0.1-5% concentration of Benzalkonium chloride; 0.2-8% concentration of 2-bromo-2-nitropropane-1,3-diol; 2-10% concentration of Disodium cocoamphoacetate OR coconut oil; 0.1-10% concentration of Citric acid; and a 10-40% concentration of Purified water.

11. An assembly for the thermal treatment, moisture treatment, and/or medicated treatment of physical conditions, comprising:
a first thermal pack having a body;
a sleeve operatively arranged to receive the first thermal pack, the sleeve having a first surface; and,
a medicament pad arranged to be removably secured to the first surface of the sleeve; wherein the chemical composition of the medicament pad comprises: a 50% concentration of Witch hazel; 10-40% concentration of Water; 1-15% concentration of Glycerin; 1-10% concentration of Alcohol; 8-30% concentration of Propylene glycol; 0.1-10% concentration of Sodium citrate; 5-15% concentration of Diazolidinyl urea; 0.1-10% concentration of Citric acid; 0.1-2% concentration of Methyl paraben; and, a 0.1-2% concentration of Propyl paraben.

12. An assembly for the thermal treatment, moisture treatment, and/or medicated treatment of physical conditions, comprising:
a first thermal pack having a body;
a sleeve operatively arranged to receive the first thermal pack, the sleeve having a first surface; and,
a medicament pad arranged to be removably secured to the first surface of the sleeve; wherein the chemical composition of the medicament pad comprises: a 50% concentration of Witch hazel; 1-10% concentration of Aloe barbadensis leaf juice; 0.1-10% concentration of Anhydrous citric acid; 0.1-5% concentration of Capryl/capramidopropyl betaine; 5-15% concentration of Diazolidinyl urea; 1-15% concentration of Glycerin; 0.1-2% concentration of Methyl paraben; 8-30% concentration of Propylene glycol; 0.1-2% concentration of Propyl paraben; 10-40% concentration of Purified water; and, a 0.1-10% concentration of Sodium citrate.

13. An assembly for the thermal treatment, moisture treatment, and/or medicated treatment of physical conditions, comprising:
a first thermal pack having a body;
a sleeve operatively arranged to receive the first thermal pack, the sleeve having a first surface; and,
a medicament pad arranged to be removably secured to the first surface of the sleeve; wherein the chemical composition of the medicament pad instead comprises: a 2-5% concentration of Lidocaine; 20-50% concentration of Cocoa Butter and/or Lanolin; 10-50% concentration of Witch Hazel; 10-40% concentration of Water; 1-15% concentration of Glycerin; 1-10% concentration of Alcohol; 1-10% concentration of Iodopropynyl Butylcarbamate; 0.1-5% concentration of Benzalkonium Chloride; 0.1-5% concentration of 2-Bromo-2nitropropane-1; 0.1-8% concentration of 3-diol; 0.1-10% concentration of Citric Acid; 0.1-2% concentration of Sodium Acetate; and, a 1-10% concentration of *Chamomilla recutita* (Matricaria) Extract.

14. An assembly for the thermal treatment, moisture treatment, and/or medicated treatment of physical conditions, comprising:
a first thermal pack having a body;
a sleeve operatively arranged to receive the first thermal pack, the sleeve having a first surface; and,
a medicament pad arranged to be removably secured to the first surface of the sleeve; wherein the chemical composition of the medicament pad comprises: a 5-20% concentration of Benzocaine; 20-50% concentration of Cocoa Butter and/or Lanolin; 10-50% concentration of Witch Hazel; 10-40% concentration of Water; 1-15% concentration of Glycerin; 1-10% concentration of Alcohol; 0.1-5% concentration of Iodopropynyl Butylcarbamate; 0.1-5% concentration of Benzalkonium Chloride; 0.1-5% concentration of 2-Bromo-2nitropropane-1; 0.1-8% concentration of 3-diol; 0.1-10% concentration of Citric Acid; 0.1-2% concentration of Sodium Acetate; and, a 1-10% concentration of *Chamomilla recutita* (Matricaria) Extract.

15. An assembly for the thermal treatment, moisture treatment, and/or medicated treatment of physical conditions, comprising:
a first thermal pack having a body;
a sleeve operatively arranged to receive the first thermal pack, the sleeve having a first surface; and,
a medicament pad arranged to be removably secured to the first surface of the sleeve; wherein the chemical composition of the medicament pad comprises: a 0.1-3% concentration of Camphor OR 1-5% concentration of Juniper tar; 20-50% concentration of Cocoa Butter and/or Lanolin; 10-50% concentration of Witch Hazel; 10-40% concentration of Water; 1-15% concentration of Glycerin; 1-10% concentration of Alcohol 1-10%; 0.1-5% concentration of Iodopropynyl Butylcarbamate; 0.1-5% concentration of Benzalkonium Chloride; 0.1-5% concentration of 2-Bromo-2nitropropane-1; 0.1-8% concentration of 3-diol; 0.1-10% Citric Acid; 0.1-2% Sodium Acetate; and, a 1-10% concentration of *Chamomilla recutita* (Matricaria) Extract.

16. An assembly for the thermal treatment, moisture treatment, and/or medicated treatment of physical conditions, comprising:
a first thermal pack having a body;
a sleeve operatively arranged to receive the first thermal pack, the sleeve having a first surface; and,
a medicament pad arranged to be removably secured to the first surface of the sleeve; wherein the chemical composition of the medicament pad comprises: a 1-10% concentration of Epson Salt; 10-50% concentration of Witch Hazel; 12-30% concentration of Cocoa butter; 2-10% concentration of Propylene glycol; 1-10% concentration of *Chamomilla recutita* (Matricaria) Extract; 0.1-5% concentration of Benzalkonium chloride; 0.2-8% concentration of 2-bromo-2-nitropropane-1, 3-diol; 2-10% concentration of Disodium cocoamphoacetate or Coconut oil; 0.1-10% concentration of Citric acid; and a 10-40% concentration of Purified water.

17. An assembly for the thermal treatment, moisture treatment, and/or medicated treatment of physical conditions, comprising:
a first thermal pack having a body;
a sleeve operatively arranged to receive the first thermal pack, the sleeve having a first surface; and,
a medicament pad arranged to be removably secured to the first surface of the sleeve; wherein the chemical composition of the medicament pad instead comprises: a 1-10% concentration of Epson Salt; 50% concentration of Cocoa butter; 2-10% concentration of Propylene glycol; 1-10% concentration of *Chamomilla recutita* (Matricaria) Extract; 0.1-5% concentration of Benzalkonium chloride; 0.2-8% concentration of 2-bromo-2-nitropropane-1, 3-diol; 2-10% concentration of Disodium cocoamphoacetate or Coconut oil; 0.1-10% concentration of Citric acid; and, a 10-40% concentration of Purified water.

* * * * *